United States Patent
Krumme et al.

(10) Patent No.: US 12,064,156 B2
(45) Date of Patent: Aug. 20, 2024

(54) DYNAMIC COMPRESSION FIXATION DEVICES

(71) Applicants: John F. Krumme, Bainbridge Island, WA (US); Karl Krumme, Bainbridge Island, WA (US)

(72) Inventors: John F. Krumme, Bainbridge Island, WA (US); Karl Krumme, Bainbridge Island, WA (US)

(73) Assignee: John F. Krumme, Bainbridge Island, WA (US)

(*) Notice: Subject to any disclaimer, the term of this patent is extended or adjusted under 35 U.S.C. 154(b) by 0 days.

(21) Appl. No.: 18/152,010

(22) Filed: Jan. 9, 2023

(65) Prior Publication Data
US 2024/0225708 A1   Jul. 11, 2024

(51) Int. Cl.
*A61B 17/84* (2006.01)
*A61B 17/86* (2006.01)
*A61B 17/68* (2006.01)

(52) U.S. Cl.
CPC .......... *A61B 17/863* (2013.01); *A61B 17/864* (2013.01); *A61B 17/8685* (2013.01); *A61B 2017/681* (2013.01)

(58) Field of Classification Search
CPC .. A61B 17/844; A61B 17/864; A61B 17/8685
See application file for complete search history.

(56) References Cited

U.S. PATENT DOCUMENTS

| | | | |
|---|---|---|---|
| 2,704,112 | A | 3/1955 | Rice |
| 3,229,954 | A | 1/1966 | Hendricks |
| 4,468,201 | A | 8/1984 | Fukuyo |
| 4,959,064 | A | 9/1990 | Engelhardt |
| 4,971,344 | A | 11/1990 | Turner |
| 5,108,289 | A | 4/1992 | Fukuyo |
| 5,120,175 | A | 6/1992 | Arbegast et al. |
| 5,184,703 | A | 2/1993 | Van Zeggeren |
| 5,229,562 | A | 7/1993 | Burnett et al. |
| 5,306,310 | A | 4/1994 | Siebels |
| 5,356,413 | A | 10/1994 | Martins et al. |
| 5,368,358 | A | 11/1994 | Christensen |
| 5,397,331 | A | 3/1995 | Himpens et al. |
| 5,417,712 | A | 5/1995 | Whittaker et al. |
| 5,423,817 | A | 6/1995 | Lin |

(Continued)

FOREIGN PATENT DOCUMENTS

| | | |
|---|---|---|
| EP | 108327 B1 | 4/1988 |
| EP | 0680351 B1 | 8/1998 |

(Continued)

*Primary Examiner* — Nicholas W Woodall
(74) *Attorney, Agent, or Firm* — Shay Glenn LLP

(57) ABSTRACT

Devices and methods are disclosed for orthopedic uses, such as treating and compressing a broken bone. An implantable device may be provided with an elongate body, a head region, a bone engagement part such as an anchor region or threads, a dynamic compression portion in either a first axially compact configuration or a second axially elongated configuration and configured to transform between the first axially compact configuration and the second axially elongated configuration, and a sleeve slidably located over the dynamic compression portion and configured to inhibit the dynamic compression portion from expanding radially outward.

19 Claims, 25 Drawing Sheets

(56) References Cited

U.S. PATENT DOCUMENTS

| | | | |
|---|---|---|---|
| 5,571,104 A | 11/1996 | Li | |
| 5,702,397 A | 12/1997 | Gobel et al. | |
| 5,733,307 A | 3/1998 | Dinsdale | |
| 5,791,899 A | 8/1998 | Sachdeva et al. | |
| 5,833,699 A | 11/1998 | Chuter | |
| 5,833,705 A | 11/1998 | Ken et al. | |
| 5,876,434 A | 3/1999 | Flomenblit et al. | |
| 5,964,770 A | 10/1999 | Flomenblit et al. | |
| 6,030,162 A | 2/2000 | Huebner | |
| 6,053,992 A | 4/2000 | Wu et al. | |
| 6,182,929 B1 | 2/2001 | Martin et al. | |
| 6,290,719 B1 | 9/2001 | Garberoglio | |
| 6,315,796 B1 | 11/2001 | Eaton | |
| 6,325,830 B1 | 12/2001 | Mastrorio et al. | |
| 6,337,142 B2 | 1/2002 | Harder et al. | |
| 6,355,039 B1 | 3/2002 | Troussel et al. | |
| 6,447,524 B1 | 9/2002 | Knodel et al. | |
| 6,485,524 B2 | 11/2002 | Strecker | |
| 6,527,774 B2 | 3/2003 | Lieberman | |
| 6,544,265 B2 | 4/2003 | Lieberman | |
| 6,551,319 B2 | 4/2003 | Lieberman | |
| 6,554,833 B2 | 4/2003 | Levy et al. | |
| 6,562,071 B2 | 5/2003 | Jarvinen | |
| 6,585,719 B2 | 7/2003 | Wang | |
| 6,656,184 B1 | 12/2003 | White et al. | |
| 6,689,154 B2 | 2/2004 | Bartlett | |
| 6,726,696 B1 | 4/2004 | Houser et al. | |
| 6,770,094 B2 | 8/2004 | Fehling et al. | |
| 6,773,437 B2 | 8/2004 | Ogilvie et al. | |
| 6,833,006 B2 | 12/2004 | Foley et al. | |
| 6,872,433 B2 | 3/2005 | Seward et al. | |
| 7,073,504 B2 | 7/2006 | Callister et al. | |
| 7,077,867 B1 | 7/2006 | Pope et al. | |
| 7,149,587 B2 | 12/2006 | Wardle et al. | |
| 7,175,626 B2 | 2/2007 | Neff | |
| 7,285,087 B2 | 10/2007 | Moaddeb et al. | |
| 7,311,313 B1 | 12/2007 | Ray et al. | |
| 7,416,534 B2 | 8/2008 | Nair et al. | |
| 7,455,356 B2 | 11/2008 | Park | |
| 7,478,803 B2 | 1/2009 | Lee | |
| 7,531,004 B2 | 5/2009 | Bagga et al. | |
| 7,559,942 B2 * | 7/2009 | Paul | A61B 17/7023 606/257 |
| 7,585,316 B2 | 9/2009 | Trieu | |
| 7,621,912 B2 | 11/2009 | Harms et al. | |
| 7,621,940 B2 | 11/2009 | Harms et al. | |
| 7,651,528 B2 | 1/2010 | Montgomery et al. | |
| 7,691,461 B1 | 4/2010 | Prabhu | |
| 7,695,471 B2 | 4/2010 | Cheung et al. | |
| 7,708,704 B2 | 5/2010 | Mitelberg et al. | |
| 7,735,909 B2 | 6/2010 | Satou et al. | |
| 7,763,073 B2 | 7/2010 | Hawkins et al. | |
| 7,785,317 B2 | 8/2010 | Mitelberg | |
| 7,862,063 B2 | 1/2011 | Stumm et al. | |
| 7,867,278 B2 | 1/2011 | Lambrecht et al. | |
| 7,875,059 B2 | 1/2011 | Patterson et al. | |
| 7,875,070 B2 | 1/2011 | Molaei | |
| 7,905,908 B2 * | 3/2011 | Cragg | A61F 2/4425 606/279 |
| 7,947,135 B2 | 5/2011 | Fonte | |
| 7,985,222 B2 | 7/2011 | Gall et al. | |
| 8,048,080 B2 | 11/2011 | Bleich et al. | |
| 8,048,134 B2 | 11/2011 | Partin | |
| 8,062,325 B2 | 11/2011 | Mitelberg et al. | |
| 8,105,368 B2 * | 1/2012 | Jackson | A61B 17/7008 606/326 |
| 8,128,698 B2 | 3/2012 | Bentley et al. | |
| 8,292,932 B2 | 10/2012 | Matthis et al. | |
| 8,298,287 B2 | 10/2012 | Moumene et al. | |
| 8,323,272 B2 | 12/2012 | Rusly et al. | |
| 8,348,994 B2 | 1/2013 | Leopold et al. | |
| 8,394,097 B2 | 3/2013 | Peyrot et al. | |
| 8,444,682 B2 | 5/2013 | Yeung et al. | |
| 8,449,574 B2 | 5/2013 | Biedermann et al. | |
| 8,454,653 B2 | 6/2013 | Hadba et al. | |
| 8,454,655 B2 | 6/2013 | Yeung et al. | |
| 8,486,121 B2 | 7/2013 | Biedermann et al. | |
| 8,491,637 B2 | 7/2013 | Matthis et al. | |
| 8,500,780 B2 | 8/2013 | Petit et al. | |
| 8,518,084 B2 | 8/2013 | Biedermann et al. | |
| 8,632,570 B2 | 1/2014 | Biedermann et al. | |
| 8,641,734 B2 | 2/2014 | Moumene et al. | |
| 8,721,646 B2 | 5/2014 | Fox | |
| 8,721,650 B2 | 5/2014 | Fanton et al. | |
| 8,740,987 B2 | 6/2014 | Geremakis et al. | |
| 8,808,272 B2 | 8/2014 | Barry et al. | |
| 8,864,159 B2 | 10/2014 | Scolari | |
| 9,017,331 B2 | 4/2015 | Fox | |
| 9,039,766 B1 | 5/2015 | Fonte | |
| 9,089,407 B2 | 7/2015 | Schaer et al. | |
| 9,107,679 B2 | 8/2015 | Lang et al. | |
| 9,138,274 B1 | 9/2015 | Biesinger et al. | |
| 9,168,074 B2 | 10/2015 | Prandi et al. | |
| 9,204,915 B2 | 12/2015 | Arthur et al. | |
| 9,216,100 B2 | 12/2015 | Seibold et al. | |
| 9,259,337 B2 | 2/2016 | Cox et al. | |
| 9,278,000 B2 | 3/2016 | Fonte et al. | |
| 9,283,006 B2 | 3/2016 | Fonte | |
| 9,283,007 B2 | 3/2016 | Augoyard et al. | |
| 9,326,804 B2 | 5/2016 | Biedermann et al. | |
| 9,433,451 B2 * | 9/2016 | Ehmke | A61B 17/744 |
| 9,480,574 B2 | 11/2016 | Lee et al. | |
| 9,492,215 B2 | 11/2016 | Augoyard et al. | |
| 9,498,348 B2 | 11/2016 | Dix | |
| 9,522,019 B2 | 12/2016 | Biedermann | |
| 9,554,915 B2 | 1/2017 | McCormick et al. | |
| 9,566,840 B2 | 2/2017 | Seethaler et al. | |
| 9,656,743 B2 | 5/2017 | Rawlings et al. | |
| 9,657,771 B1 | 5/2017 | Trout | |
| 9,693,765 B2 | 7/2017 | Sullivan et al. | |
| 9,724,138 B2 | 8/2017 | Palmer et al. | |
| 9,759,203 B2 | 9/2017 | Brown | |
| 9,814,499 B2 | 11/2017 | Buscaglia et al. | |
| 9,861,412 B2 | 1/2018 | Biedermann et al. | |
| 9,861,413 B2 | 1/2018 | Palmer et al. | |
| 9,956,012 B2 | 5/2018 | Biedermann et al. | |
| 9,980,715 B2 | 5/2018 | Marino et al. | |
| 10,012,621 B2 | 7/2018 | Dehmer | |
| 10,030,333 B2 | 7/2018 | Bertelo et al. | |
| 10,072,724 B2 | 9/2018 | Haugen | |
| 10,117,647 B2 | 11/2018 | Cheney | |
| 10,130,358 B2 | 11/2018 | Palmer et al. | |
| 10,130,530 B2 | 11/2018 | Golden | |
| 10,136,929 B2 | 11/2018 | Fallin et al. | |
| 10,154,863 B2 | 12/2018 | Fallin et al. | |
| 10,182,822 B2 | 1/2019 | Freudenthal | |
| 10,195,034 B2 | 2/2019 | Colombo et al. | |
| 10,245,017 B2 | 4/2019 | Stone | |
| 10,253,419 B2 | 4/2019 | Lomasney | |
| 10,259,520 B2 | 4/2019 | Butora et al. | |
| 11,317,956 B1 | 5/2022 | Gregersen et al. | |
| 2002/0168499 A1 | 11/2002 | Goldbach et al. | |
| 2003/0032339 A1 | 2/2003 | Bell et al. | |
| 2003/0220643 A1 * | 11/2003 | Ferree | A61B 17/7028 606/264 |
| 2004/0073216 A1 | 4/2004 | Lieberman | |
| 2004/0097939 A1 | 5/2004 | Bonutti | |
| 2004/0138707 A1 | 7/2004 | Greenhalgh | |
| 2004/0193257 A1 | 9/2004 | Wu et al. | |
| 2004/0225361 A1 | 11/2004 | Glenn et al. | |
| 2004/0236328 A1 | 11/2004 | Paul et al. | |
| 2005/0154390 A1 * | 7/2005 | Biedermann | A61B 17/7028 606/279 |
| 2005/0205364 A1 | 9/2005 | Browne et al. | |
| 2005/0283159 A1 | 12/2005 | Amara | |
| 2006/0095134 A1 | 5/2006 | Trieu et al. | |
| 2006/0136034 A1 | 6/2006 | Modesitt et al. | |
| 2008/0140203 A1 | 6/2008 | Davis | |
| 2008/0294204 A1 | 11/2008 | Chirico et al. | |
| 2009/0088782 A1 | 4/2009 | Moumene et al. | |
| 2009/0216334 A1 | 8/2009 | Leibel | |
| 2009/0222103 A1 | 9/2009 | Fitz et al. | |
| 2010/0211071 A1 | 8/2010 | Lettmann et al. | |
| 2010/0239883 A1 | 9/2010 | Okladek et al. | |

(56) References Cited

U.S. PATENT DOCUMENTS

| | | |
|---|---|---|
| 2011/0040383 A1 | 2/2011 | Wurfel |
| 2011/0071633 A1 | 3/2011 | Fonte |
| 2012/0172936 A1 | 7/2012 | Horrell et al. |
| 2013/0046346 A1 | 2/2013 | Thorwarth et al. |
| 2013/0067907 A1 | 3/2013 | Greene et al. |
| 2013/0211451 A1 | 8/2013 | Wales et al. |
| 2014/0094860 A1 | 4/2014 | Reimels |
| 2014/0222040 A1 | 8/2014 | Park et al. |
| 2014/0277444 A1 | 9/2014 | Clifford et al. |
| 2015/0230843 A1 | 8/2015 | Palmer et al. |
| 2015/0320413 A1 | 11/2015 | Gittings et al. |
| 2016/0038186 A1 | 2/2016 | Herzog et al. |
| 2016/0183992 A1 | 6/2016 | Huang et al. |
| 2016/0213412 A1 | 7/2016 | Palmer et al. |
| 2016/0317720 A1 | 11/2016 | Ostapoff et al. |
| 2017/0051808 A1 | 2/2017 | Bogrash et al. |
| 2017/0056229 A1 | 3/2017 | Palmer et al. |
| 2017/0100171 A1 | 4/2017 | Palmer et al. |
| 2017/0216034 A1 | 8/2017 | Daniel et al. |
| 2017/0311984 A1 | 11/2017 | Stecco et al. |
| 2017/0360489 A1 | 12/2017 | Palmer et al. |
| 2018/0078293 A1 | 3/2018 | Hustedt et al. |
| 2018/0092677 A1 | 4/2018 | Peterson et al. |
| 2018/0132916 A1 | 5/2018 | Biedermann et al. |
| 2018/0206897 A1 | 7/2018 | Palmer |
| 2018/0263669 A1 | 9/2018 | Peterson et al. |
| 2018/0344316 A1 | 12/2018 | Palmer et al. |
| 2019/0046182 A1 | 2/2019 | Krumme |
| 2019/0046183 A1 | 2/2019 | Hartdegen et al. |
| 2019/0184058 A1 | 6/2019 | Aihara et al. |
| 2020/0146668 A1 | 5/2020 | Krumme |
| 2020/0155298 A1 | 5/2020 | Krumme et al. |
| 2020/0305938 A1* | 10/2020 | Krumme ............ A61B 17/8625 |
| 2022/0142691 A1* | 5/2022 | Smith ................ A61B 17/8685 |
| 2022/0218400 A1 | 7/2022 | Krumme et al. |
| 2022/0313239 A1 | 10/2022 | Krumme |

FOREIGN PATENT DOCUMENTS

| | | |
|---|---|---|
| EP | 1239151 A1 | 11/2002 |
| EP | 1524450 A1 | 4/2005 |
| EP | 1582163 A1 | 10/2005 |
| EP | 1913887 A1 | 4/2008 |
| EP | 1531765 B1 | 7/2008 |
| EP | 1699681 B1 | 6/2010 |
| EP | 2698310 B1 | 5/2018 |
| JP | H04-145286 A | 5/1992 |
| KR | 10-2015-0030330 A | 3/2015 |
| WO | WO99/67548 A2 | 12/1999 |
| WO | WO2018/071490 A1 | 4/2018 |
| WO | WO2019/108222 A1 | 6/2019 |
| WO | WO2019/113115 A1 | 6/2019 |
| WO | WO2023/178321 A2 | 9/2023 |

* cited by examiner

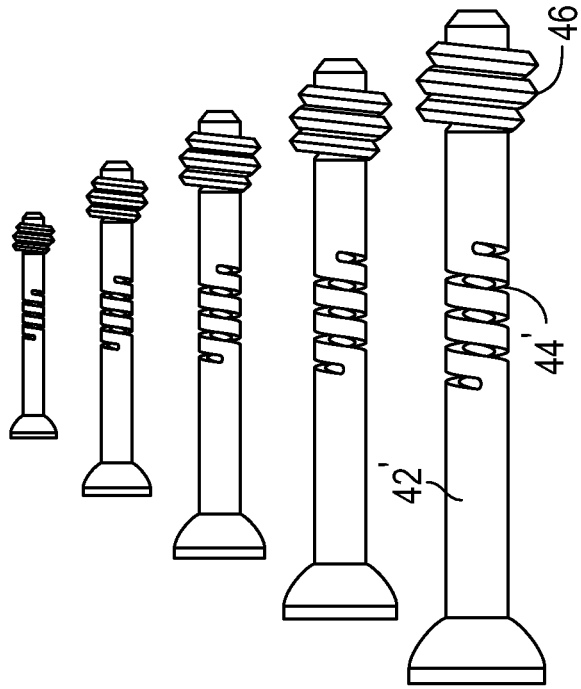
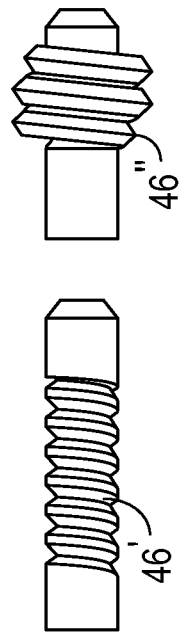
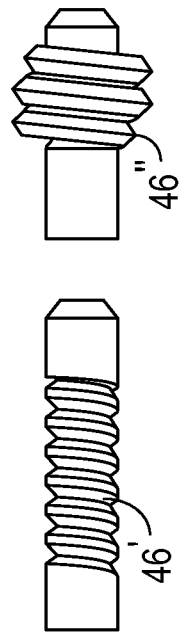
FIG. 6D
FIG. 6E
FIG. 6F
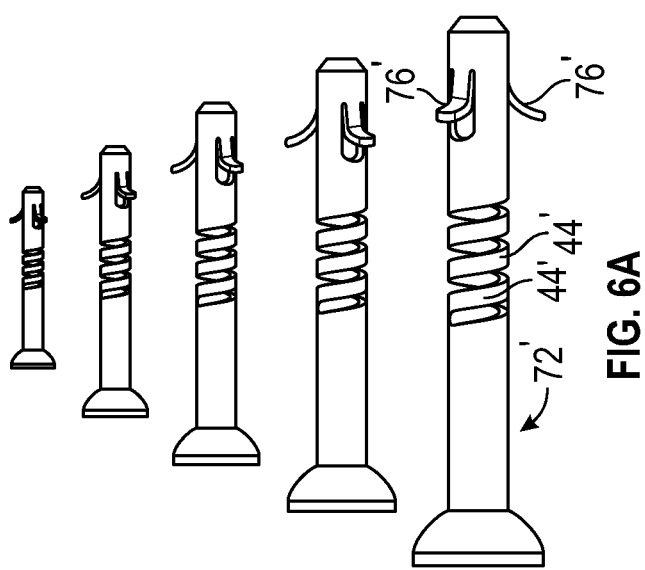
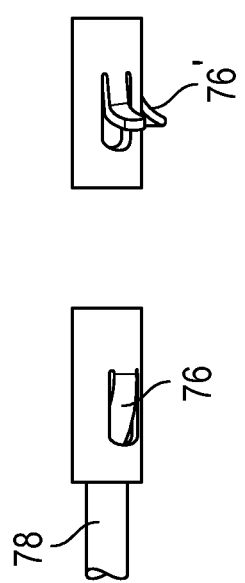
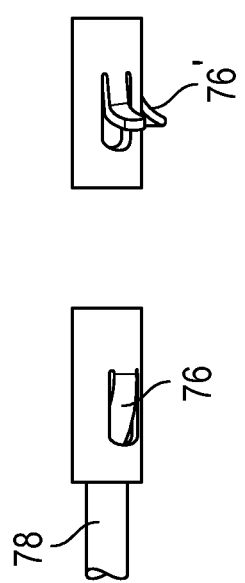
FIG. 6A
FIG. 6B
FIG. 6C

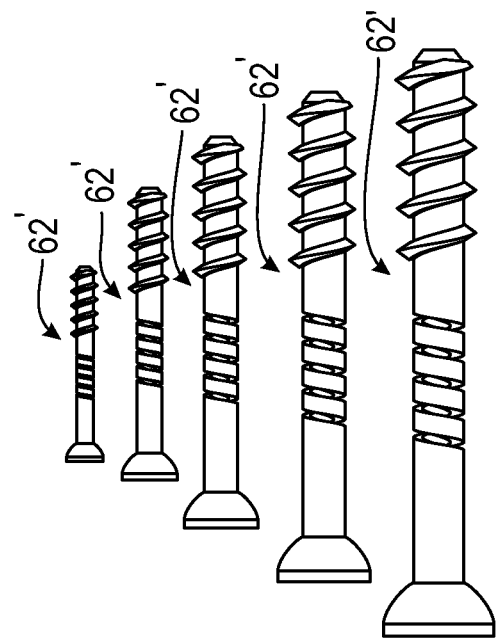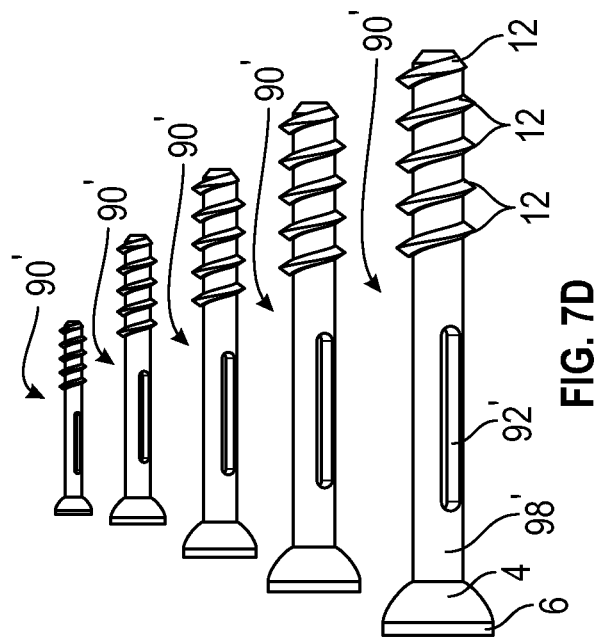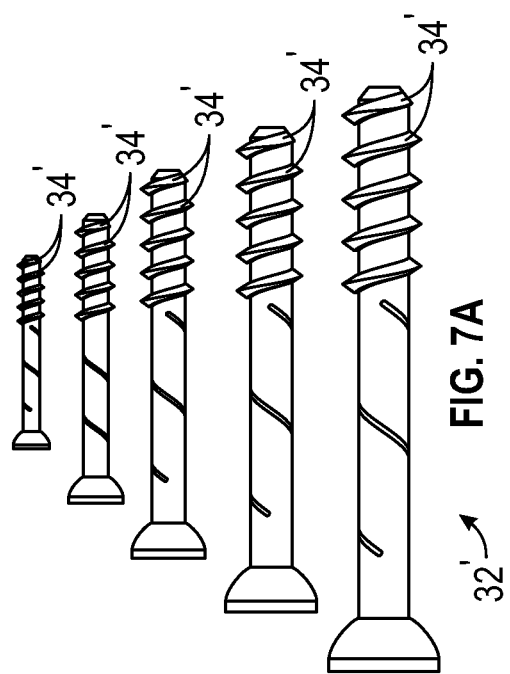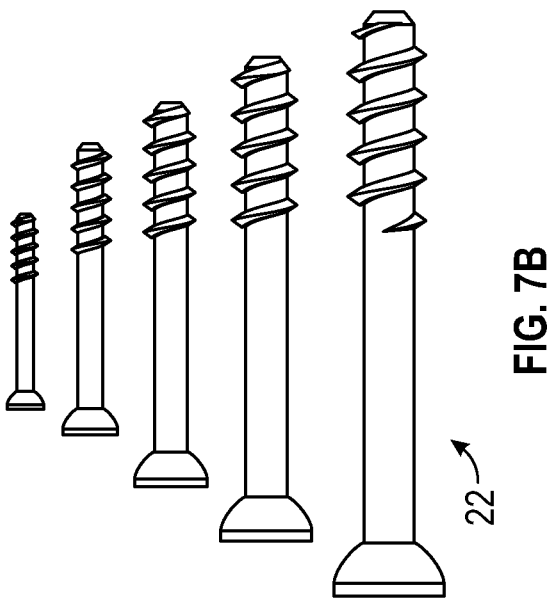

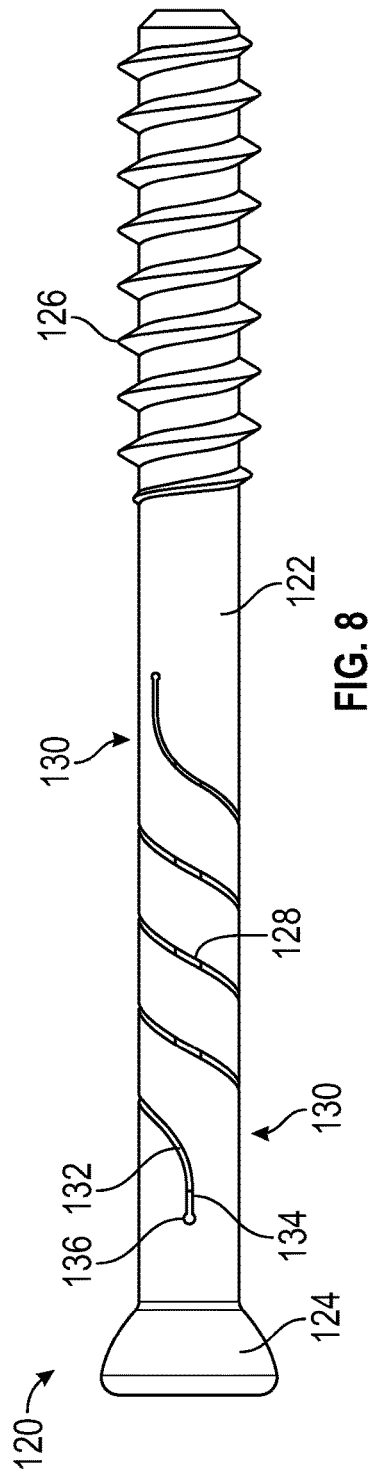
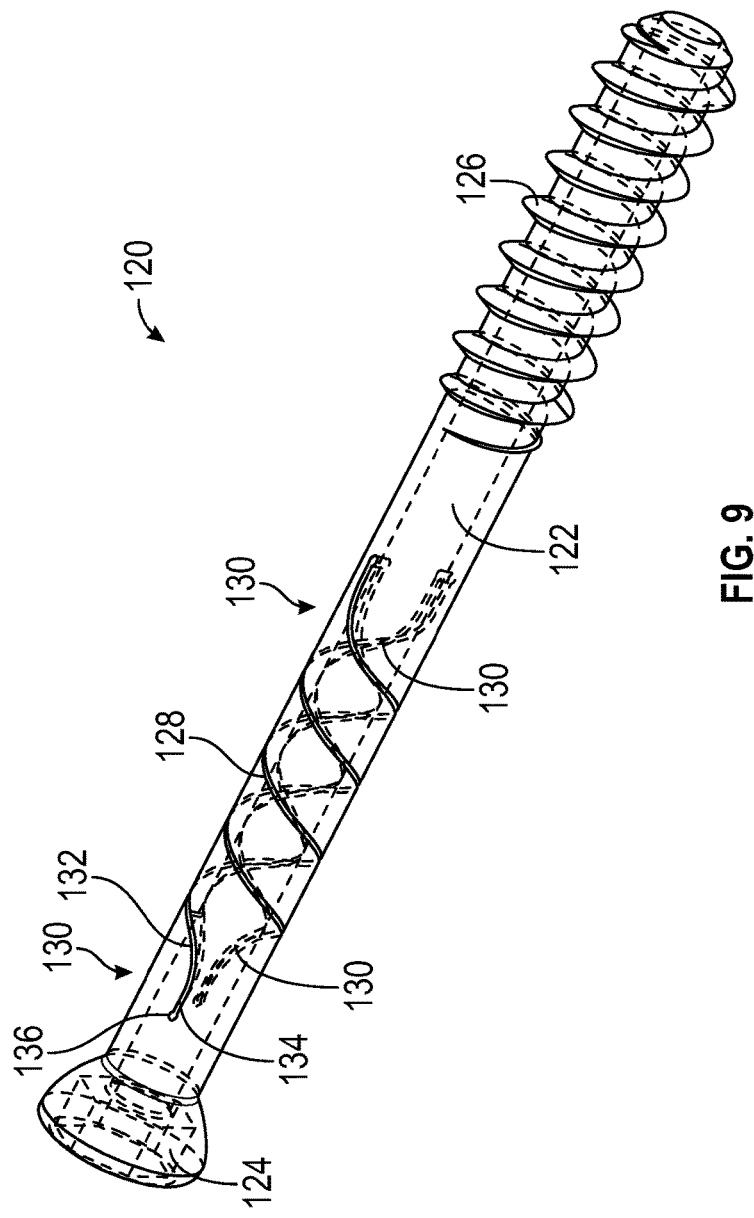
FIG. 8
FIG. 9

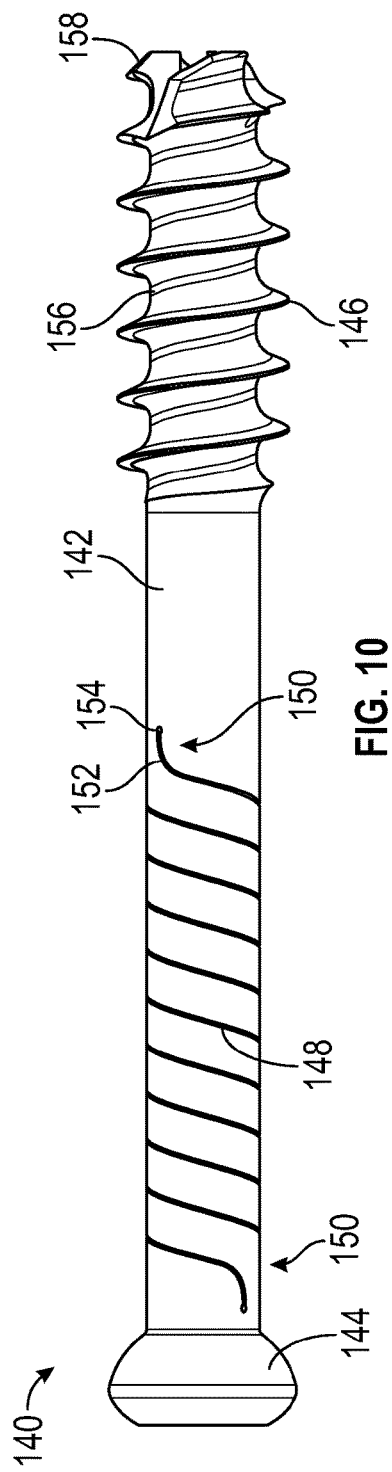
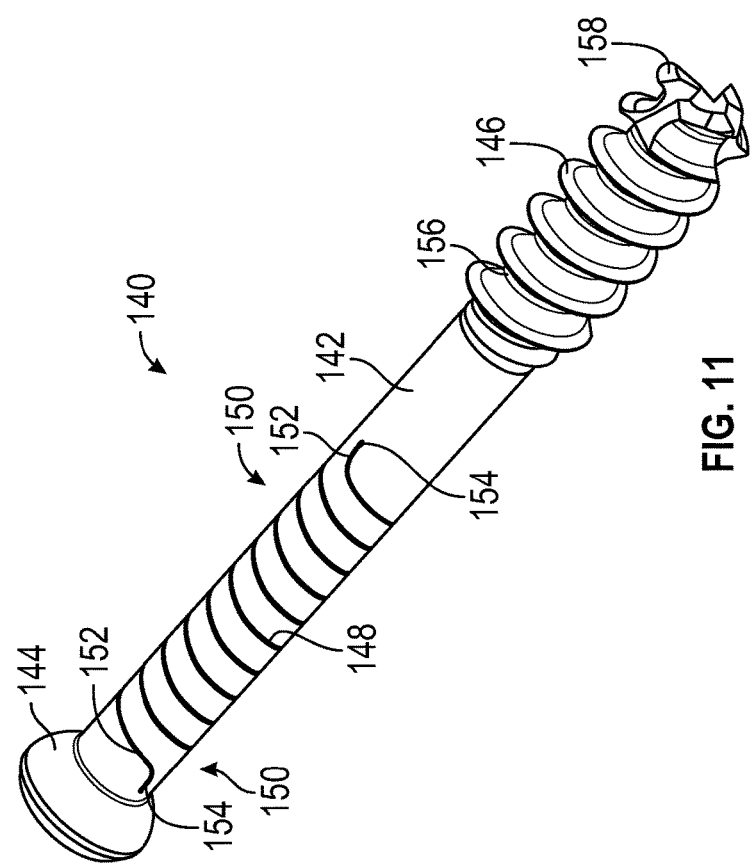
FIG. 10
FIG. 11

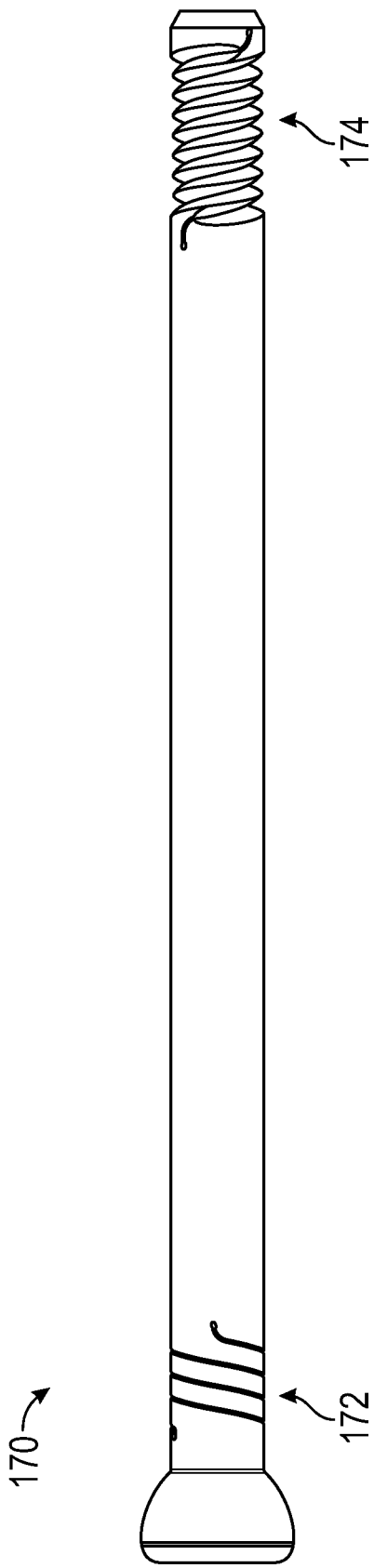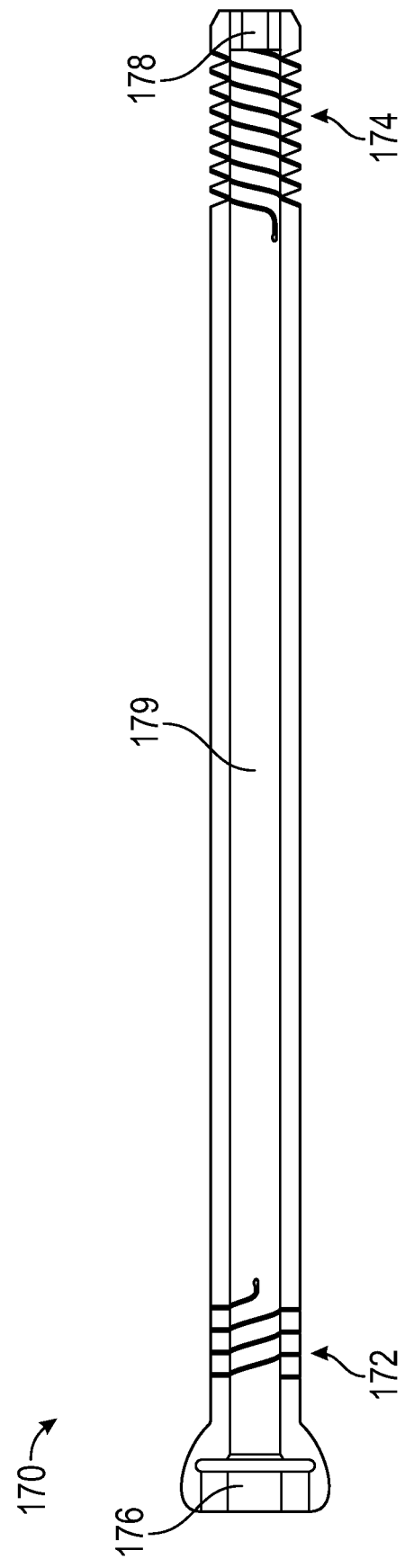

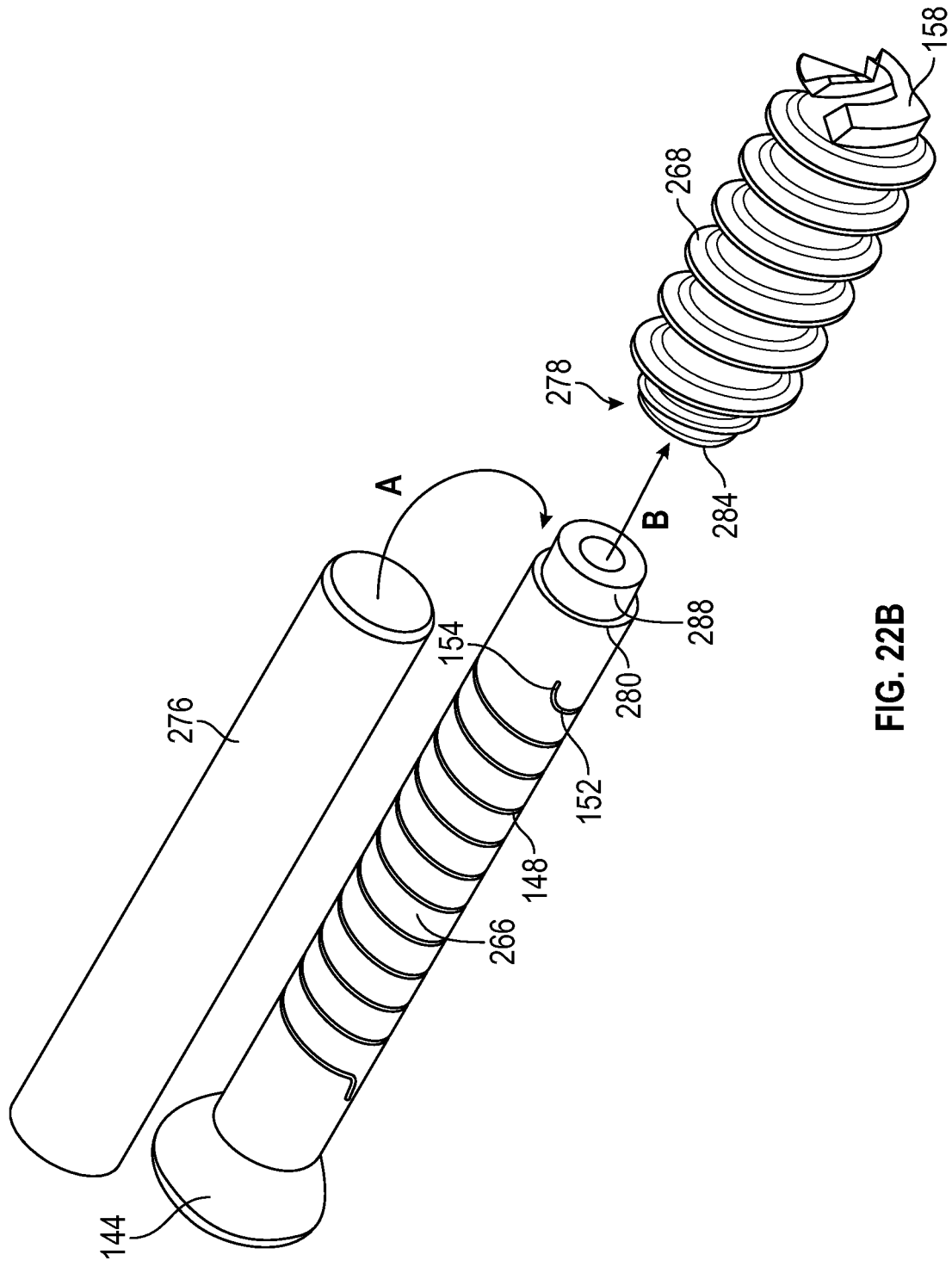

DYNAMIC COMPRESSION FIXATION DEVICES

CROSS REFERENCE TO RELATED APPLICATIONS

None.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure is related to implantable devices, especially implantable devices for orthopedic uses. In particular this disclosure is related to implantable devices that may provide dynamic compression to a broken bone.

BACKGROUND

The skeletal system of the body includes 206 bones and numerous joints. The bones and joints act as a scaffold by providing support and protection for the soft tissues. The bones and joints are also necessary for body movement. The bones of the skeletal system are made up of calcium and minerals, as well as cells and proteins. Bones can be broken due to trauma or force, such as falling on a sidewalk or being hit by a car. Various physiological processes in the body act to heal broken bones. Starting from soft, inflamed, swollen tissue at the bone fracture site, the body's natural process of healing a bone fracture includes a healing progression that takes place over the course of a number of weeks or months. After an initial inflammation, the process moves to repairing the damage, and finally moves on to remodeling the bone. The average time to heal a broken bone is between 6-8 weeks (and longer if full reshaping is considered), although the actual amount of time varies depending on a number of factors specific to the injury, including type of injury, the site of the injury, the grade of the injury, other tissue damage, and the age and health of the patient. Although a continuous process, average bone fracture healing can be divided into a number of stages based on the physiological healing process, including inflammation and hematoma formation (0-2 weeks), soft callus formation (2-3 weeks), hard callus formation (3-6 weeks), and bone remodeling (8 weeks-2 years).

Common practices in bone fracture treatments include providing compression to and stabilization of the broken bone. Some bone fracture treatments include non-surgical approaches, such as using splints to minimize movement, braces to support the bone, or casts to support and immobilize the bone. Some bone fracture treatments are surgical and involve surgically inserting implants in or around the bones. For treating some bone fractures, special screws are placed in the broken bone to hold the broken pieces close together. For treating some bone fractures, such as fractures of the thigh bone or shin bone, a special plate called a bone plate may be placed on the fractured bone segments to stabilize, protect, and align the fractured bone segments for healing. The bone plate can be held on the bone with screws that screw into the bone. To stabilize some fractures, a long rod, called an intramedullary rod, may be placed inside the bone. The intramedullary rod may be held inside the bone using screws screwed through the rod and the bone.

According to the American Academy of Orthopaedic Surgeons, an average of more than 6 million people in the United States break a bone every year. Although many of these broken bones heal properly, many others do not. It is estimated that of those broken bones, up to 20% will not heal properly. Improper healing includes delayed union (the fractured bone takes longer than usual to heal), malunion (the fractured bone heals in an abnormal position), and nonunion (the fracture does not heal). A number of factors can contribute to improper healing, and it is generally thought that bone misalignment during the weeks-long healing process is a major contributor to improper healing. Improper healing of broken bones can result in loss of function, decreased quality of life, swelling, chronic pain, inability to work, limited ability to work or recreate, and additional medical and hospital costs.

Thus, there is a need for improved devices and methods to improve outcomes for patients with broken bones. Described herein are apparatuses and methods that may address these and other problems.

SUMMARY OF THE DISCLOSURE

The present disclosure relates to apparatuses (devices and methods) for orthopedic uses. In particular this disclosure is related to implantable devices that may provide dynamic compression to a broken bone. Described herein is an implantable device including an elongate body with a proximal end and a distal end, the elongate body including a head region at the proximal end of the elongate body; a bone engagement part at the distal end of the elongate body; a cannulated rod connecting the head region and the bone engagement region, wherein the cannulated rod can include a dynamic compression portion between the head region and the bone engagement part, the dynamic compression portion in either (i) a first axially compact configuration or (ii) a second axially elongated configuration, wherein the dynamic compression portion can include a material configured to transform between the first, axially compact configuration and the second, axially elongated configuration; and a sleeve over the dynamic compression portion, the sleeve having a proximal end and a distal end.

This and other embodiments can include one or more of the following features. An outside diameter of the dynamic compression portion and an inside diameter of the sleeve can be in contact. The implantable device can include a gap of at least 0.002 inches between an outside diameter of the dynamic compression portion and an inside diameter of the sleeve. An outside diameter of the dynamic compression portion and an inside diameter of the sleeve can be not more than 0.020 inches apart.

This and other embodiments can include one or more of the following features. The sleeve can substantially surround an outside of the dynamic compression portion. The sleeve can be attached to the elongate body. The sleeve can be attached to the cannulated rod. The proximal end of the sleeve can be attached to a proximal end of the elongate body. The distal end of the sleeve can be attached to the distal end of the elongate body. The sleeve can be unattached to the elongate body and can be configured to move over the elongate body.

This and other embodiments can include one or more of the following features. The dynamic compression zone and bone engagement part can include a shape memory material. The dynamic compression zone and bone engagement part can include nitinol. The sleeve can include nitinol. The sleeve can include titanium or PEEK. The sleeve can not include nitinol (the sleeve can exclude nitinol).

This and other embodiments can include one or more of the following features. The cannulated rod can include a rod wall and a first helical slit through the rod wall. The cannulated rod can include a second helical slit in the rod wall. The first and second helical slits can be wrapped around a single length of a central zone of the dynamic compression portion, and/or the dynamic compression portion can be separated from the bone engagement part by an unthreaded intervening portion therebetween.

This and other embodiments can include one or more of the following features. The dynamic compression portion further can include (i) a first, radially compact configuration or (ii) a second, radially expanded configuration, wherein the material in the dynamic compression portion is configured to transform between the first, radially compact configuration and the second radially expanded configuration.

In general, an implantable device includes an elongate body with a proximal end and a distal end, the elongate body including a head region at the proximal end of the elongate body; a bone engagement part at the distal end of the elongate body; a cannulated rod connecting the head region and the bone engagement region, wherein the cannulated rod can includes a dynamic compression portion between the head region and the bone engagement part, the dynamic compression portion in either (i) a first axially compact configuration or (ii) a second axially elongated configuration, wherein the dynamic compression portion can includes a material configured to transform between the first, axially compact configuration and the second, axially elongated configuration; and a sleeve over the dynamic compression portion, the sleeve having a proximal end and a distal end.

This and other embodiments can include one or more of the following features. The bone engagement part can include a screw thread configured to anchor the implantable device into a bone segment.

This and other embodiments can include one or more of the following features. The second, elongated configuration can be at least 0.5% longer than the first, compact configuration. This and other embodiments can include one or more of the following features. The dynamic compression portion can include a cannulated rod with a rod wall and a helical slit through a wall thickness thereof. The helical slit can be provided with an end geometry that is different from a middle portion of the helical slit. The end geometry can include a curved portion and a straight portion, and the straight portion can generally align with a longitudinal axis of the implantable device, and the curved portion can transition a trajectory of the helical slit between a normal pitch to a direction of the straight portion. The curved portion and the straight portion can cooperate to dissipate stresses that may be concentrated at an end of the helical cut.

In general, a method of withdrawing an implantable device from a substrate includes the steps of engaging a tool with the implantable device, wherein the implantable device includes an elongate body with a proximal end and a distal end, wherein the elongate body includes a head region at the proximal end of the elongate body; a bone engagement part at the distal end of the elongate body; a cannulated rod connecting the head region and the bone engagement region, wherein the cannulated rod includes a dynamic compression portion between the head region and the bone engagement part; a sleeve over the dynamic compression portion; the method including the steps of rotating the implantable device with the tool; stopping, with the sleeve, outward radial expansion of the dynamic compression portion; and withdrawing the implantable device from the substrate.

In this and other methods, the substrate can include bone.

In this and other methods, the dynamic compression portion can be in a second, radially compact configuration.

In this and other methods, the engaging step can include engaging the tool with an inside of the head region and/or the rotating step can include rotating the head region with the tool and thereby rotating the rest of the implantable device.

In this and other methods, the bone engagement part can include an external screw thread and the step of engaging the tool can include engaging the bone engagement part with the tool, and the method can further include a step of unscrewing the external screw thread from the substrate.

In this and other methods, the tool can include a first tool placed at the proximal end of the elongate body or at the distal end of the elongate body, the method further including a step of placing a second tool at the distal end of the elongate body or a second tool at the proximal end of the elongate body respectively, the method further including the step of engendering relative motion between the first tool and the second tool and thereby rotating the implantable device.

In this and other methods, the method can further include the step of, stopping, with the sleeve, outward radial expansion of the dynamic compression portion. This and other methods can further include, preventing, with the sleeve, the dynamic compression portion from contacting an inner wall of the substrate.

In this and other methods, the sleeve can be maintained over the dynamic compression portion by at least one attachment site between the sleeve and the elongate body.

In this and other methods, during withdrawal the dynamic compression portion axially can contract by at least 0.5% relative to the length of the axially compact configuration. In this and other methods, the elongate body axially can contract at least 0.5% relative to the length of the axially elongated configuration. This and other methods can further include the step of contracting the implantable device by at least 1% relative to the length of the axially elongated configuration toward the axially compact configuration after the implantable device has been introduced into the substrate. This and other methods can further include the step of transforming the dynamic compression portion in the sleeve from a second, radially compact configuration towards a first, radially expanded configuration.

In this and other methods, the dynamic compression portion can include a hollow region having a helical slit through a wall thickness thereof, and the method can further include the step of axially compacting the helical slit. In this and other methods, the dynamic compression portion can include a hollow region having two helical slits through a wall thickness thereof, and the method can further include the step of axially compacting both helical slits.

In this and other methods, the dynamic compression portion and bone engagement part can include nitinol.

In this and other methods, a head region at the proximal end can be wider than other portions of the elongate body and the head region can engage with a proximal end of the substrate. In this and other methods, at least a portion of the head region can remain outside the substrate. In this and other methods, at least a portion of the head region can be inside the substrate.

BRIEF DESCRIPTION OF THE DRAWINGS

The novel features of the invention are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIG. 6A shows examples of an implantable device made from a titanium alloy or stainless-steel distal anchor region.

FIG. 6B and FIG. 6C are two enlarged fragmentary views showing the distal anchor region of one of the devices from FIG. 6A, shown first with the anchors being held in a retracted state by an inserting tool (FIG. 6B), and then in a deployed state with the tool removed (FIG. 6C).

FIG. 6D shows examples of an implantable device with a proximal helix and a compressible distal threaded region.

FIG. 6E and FIG. 6F are two enlarged fragmentary views showing the distal anchor region of one of the devices from FIG. 6C, shown first with helical threads in a retracted state (FIG. 6E) and then in a deployed state (FIG. 6F).

FIG. 7A shows examples of an implantable device with a proximal helix and a distal threaded region, such as for a surgical kit.

FIG. 7B shows examples of an implantable device with a proximal elastic region and a distal threaded region, such as for a surgical kit.

FIG. 7C shows examples of an implantable device with a proximal helical region and a distal threaded region, such as for a surgical kit.

FIG. 7D shows examples of an implantable device with a proximal longitudinal slot and a distal threaded region, such as for a surgical kit.

FIG. 8 shows an example of an implantable device having helix end geometries.

FIG. 9 shows a perspective view of the device from FIG. 8.

FIG. 10 shows another example of an implantable device having helix end geometries.

FIG. 11 shows a perspective view of the device from FIG. 10.

FIG. 15 shows another example of an implantable device having helix end geometries.

FIG. 16 shows a cross-sectional view of the device from FIG. 15.

FIG. 20A shows an isometric view of an implantable device having a sleeve over a dynamically changeable helical region.

FIG. 20B shows a side view of the implantable device shown in FIG. 20A.

FIG. 20C shows an isometric view of the sleeve being placed over the longitudinal rod.

FIG. 20D shows a side view of the sleeve and longitudinal rod shown in FIG. 20C.

FIGS. 22A-22E show implantable devices with a sleeve and methods of assembling.

In these methods, a sleeve precursor is placed over a cannulated rod and then a threaded end region is attached to the cannulated rod. FIG. 22A shows an isometric view of an implantable device having a sleeve over a dynamically changeable helical region.

FIG. 22B shows an isometric view of three parts being assembled to form the implantable device shown in FIG. 22A.

FIG. 22C shows a side view of an example of a juncture made between a cannulated rod and a threaded end, such as for the implantable device shown in FIG. 22A.

FIG. 22D shows a side view of a juncture made between a cannulated rod and a threaded end in a variation of the device shown in FIG. 22A.

FIG. 22E shows a side view of a juncture being made between a cannulated rod and a threaded end such as the device shown in FIG. 22A. An assembly aid is inserted inside the channel.

DETAILED DESCRIPTION

Described herein are apparatuses and methods for orthopedic uses. In particular, described herein are implantable devices that may be especially useful for treating, repairing, or supporting a broken or damaged bone. The implantable devices may be useful for reducing bone fractures to provide proper compression and stabilization to a broken bone joint and to support joint regrowth, healing, and mechanical support during the healing process. The implantable devices may also be useful for fixing or holding another bone device, such as a bone plate or intramedullary rod, in place. The disclosure herein provides those functions and enhances bone healing rate and strength of the joint while providing better ease of use and fatigue failure resistance. As indicated above, bone fracture healing takes place in a continuous series of stages. During these stages, repair tissue for repairing the bone fracture progresses from soft tissue to a soft callus to a hard callus and then bone remodeling. The material properties of the tissue changes during these stages. As a bone fracture heals, tissues are resorbed and remodeled. Inflammation reduces. The initial placement of the segments of broken bone may have been appropriate but needs change over time and the initial placement of the bones may not be ideal over time. Although a broken bone needs to be held in place during healing, very tiny movements referred to micromovements, may aid in recovery. The implantable devices described herein may provide a better match to the material properties of healing bone over time than do existing devices. The implantable devices described herein may provide or be configured to provide appropriate dynamic compression to a fixtured bone initially as well as over an extended period of time (weeks, months, or years), as the bone heals and remodels. The implantable devices disclosed herein may provide controllable, dynamic, continuing compression to a fixtured joint and may lead to enhancing bone regrowth through modulus matched elastic properties (device to bone elastic properties); providing improved fatigue failure resistance; and in some embodiments, eliminating the twisting, screwing action and torque associated with prior art threaded screw devices made from titanium and stainless steel; and allowing micro-motion of the compressed joint for faster and stronger joint healing.

Figure 1A:
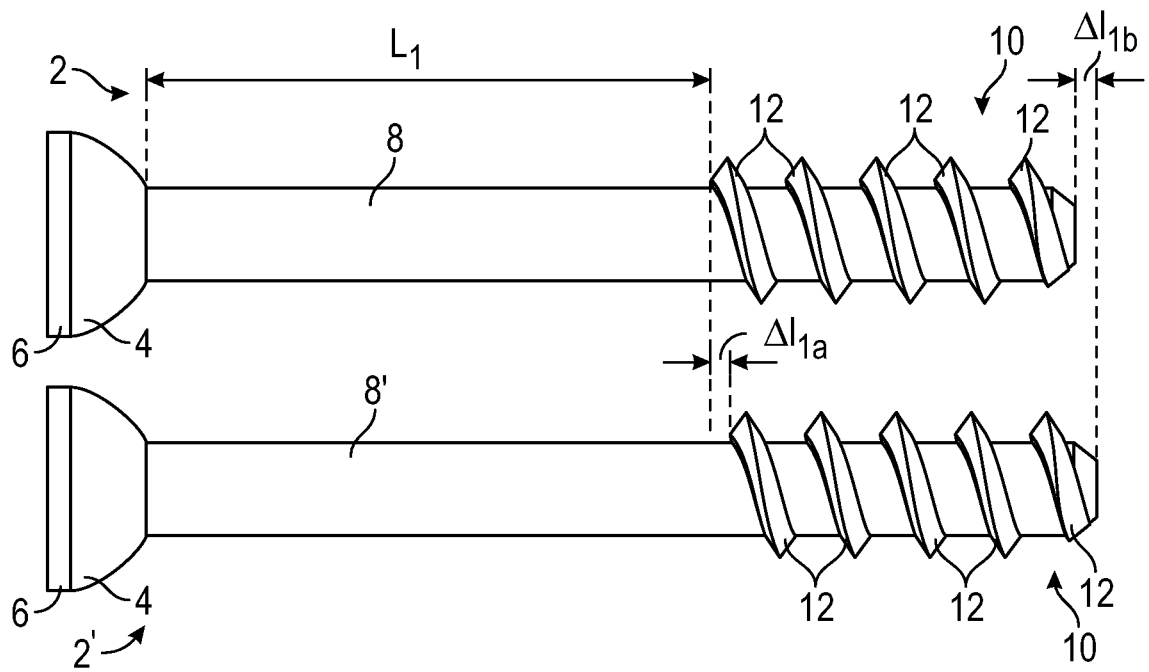
FIG. 1A shows a prior art bone screw with limited compression.
Figure 1B:
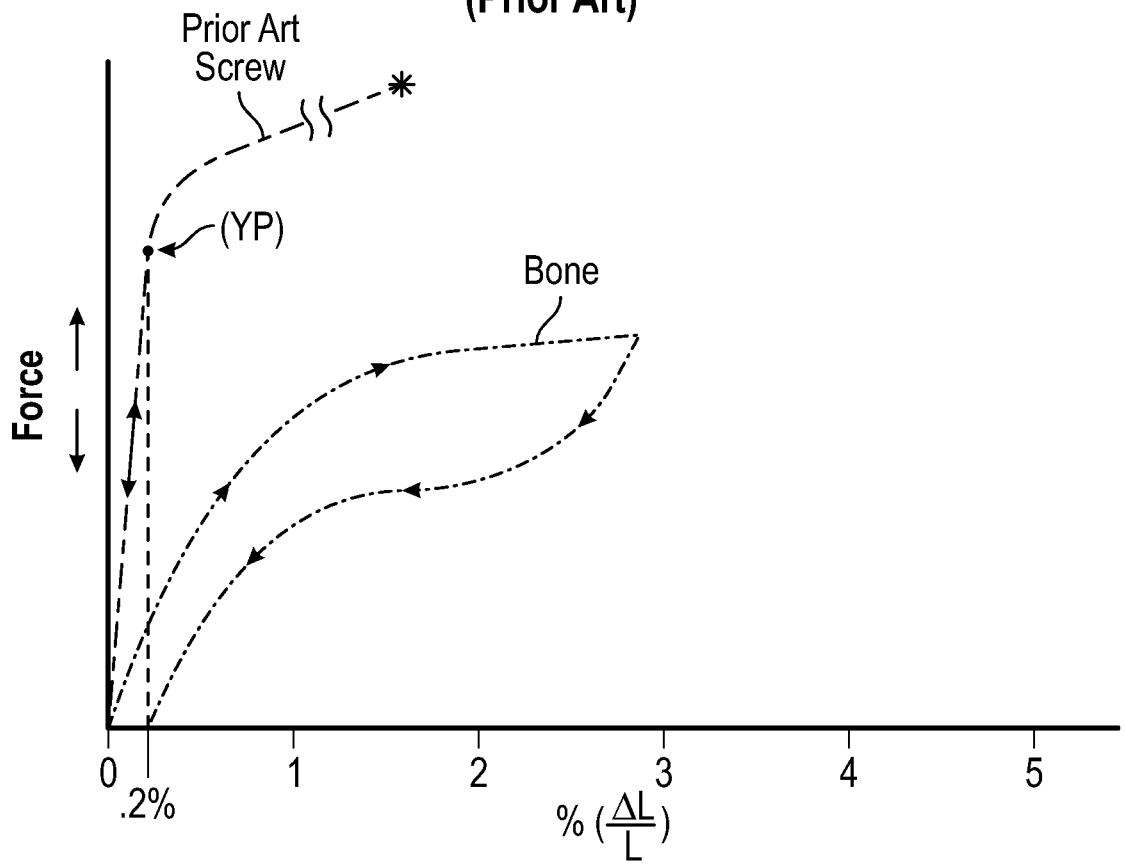
FIG. 1B shows a stress-strain graph comparing the properties of the device shown in FIG. 1A with properties of a typical bone.

FIG. 1A shows views of a prior art screw 2 (e.g., a prior art "compression" screw) as it would appear before insertion (top) and the screw 2' after insertion (bottom) across a broken bone to hold or fix the bone into position. The screw 2 has a distal threaded end 6, a smooth surfaced central axial length 8, and a proximal head 4. FIG. 1A shows the smooth surfaced central axial length 8 has a diameter smaller than the diameter of the distal threaded end 10. In use, the screw 2 is inserted into a bone by rotating a screwdriver (not shown) that engages a mating part 6 on the proximal end of the screw and rotates the screw 2 into the broken bone. The head 4 of the screw keeps the screw 2 on the outside of the bone (such as due to its wide size or a head shape that engages directly with the bone or a plate), while torque from the screwdriver causes the screw 2 to rotate into the broken bone, forcing threads 12 on the distal end 10 of the screw 2 into the bone. The screw 2 is made of implant grade titanium and/or stainless steel. As shown in FIG. 1A, as the screw 2 is inserted into the bone (not shown in this view) the torque placed on the screw threads 12 stretches the central zone 8 by a small amount $\Delta L1a$ to central zone 8' and the tip of the screw 2' extends further into the bone by the same distance, shown by $\Delta L1b$. The axial central zone can be solid or tubular but has no geometry that enhances the elastic properties of the device overall. As a result, the extent of any "compression" performance of the screw 2' is limited to the inherent low strain yield point (YP) of the titanium and/or stainless steel at 0.2%. FIG. 1B compares the stress-strain curve of force vs. % elongation for the titanium screw 2 shown in FIG. 1A with elastic properties of a typical human bone. A stainless steel screw behaves similarly to the titanium screw. Note that the "range of motion" is just 0.2% and the steep slope of the titanium/stainless steel screw does not overlay or match the bone properties graph. The initial small amount of compression provided is lost within minutes after installation. Any further rotation of the screw simply results in bone movement. At stress below the yield point (YP), the screw 2' shows elastic behavior and if stretched can return to its original size and shape. When inserted with a force below the yield point, the screw can exert compressive stress between two parts of a broken bone as it is pulled towards its original size and shape. However, if the screw is stretched beyond its yield point, the screw 2' shows permanent strain deformation (plastic behavior); it has been stretched too far and cannot return to its original size. It cannot exert a desired compressive force on the healing bone. FIG. 1B also shows the significant mismatch between the elastic properties of a typical bone and a titanium (or stainless steel) screw. Where there is a mismatch, stress on the bone is increased; the greater the mismatch, the greater the stress.

Figure 2A:
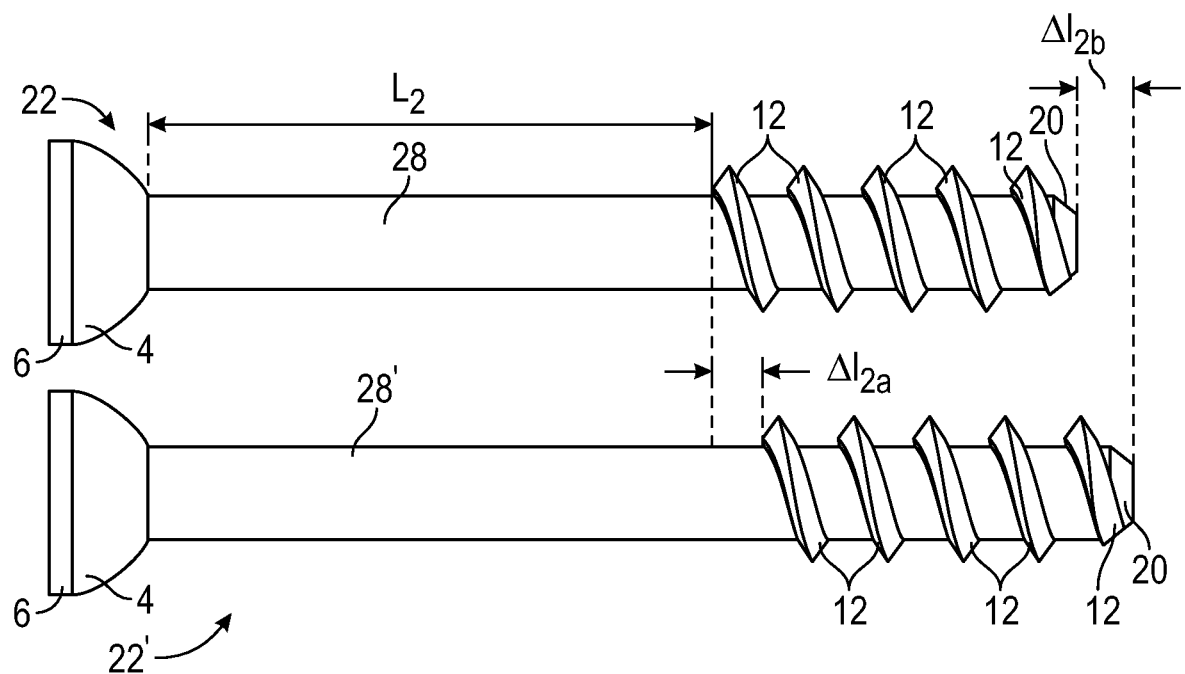
FIG. 2A shows an implantable device with dynamic compression and improved material properties.
Figure 2B:
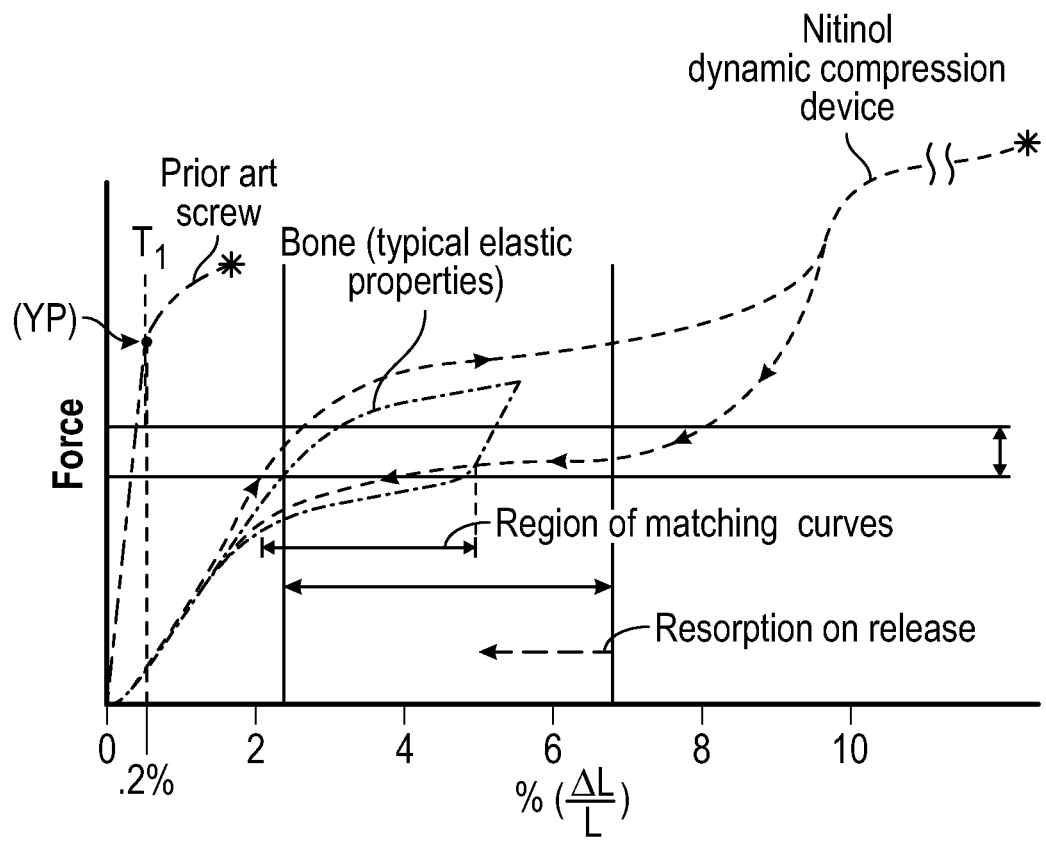
FIG. 2B shows a stress-strain graph showing the overlap in material properties of the device shown in FIG. 2A with properties of a typical bone.
Figure 2C:
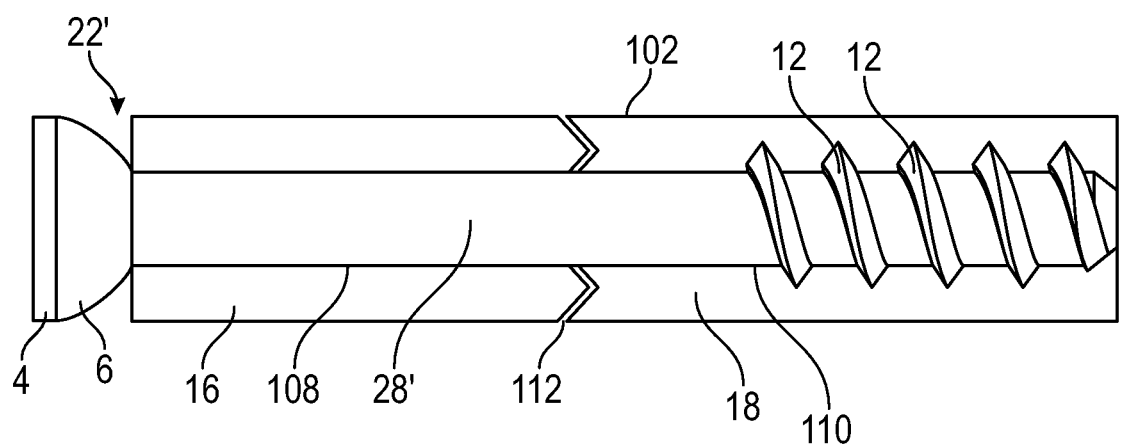
FIG. 2C shows the implantable device of FIG. 2A in place across a break in a bone.

Described herein are implantable devices, such as bone screws, with improved material properties. For example, the implantable devices may have spring-like geometry in an axial central zone and/or elastic properties closer to that of bone compared with existing devices. The implantable devices may have an elongate body with a proximal end and a distal end and a dynamic compression region (e.g., an elastic central zone) between the proximal end and the distal end. The central zone may be unthreaded and of a suitable length for the specific joint size and depth. The central zone may move between a first, axially compact configuration and a second, axially elongated configuration. The central zone may be made from an elastic material and can be considered to have "elastic stretch". FIG. 2A shows an implantable device 22 configured to deliver dynamic compression. The implantable device 22 has a head 4 at the proximal end and a distal helically threaded zone with threads 12 at the distal end 20, and a central zone 28 (e.g., a dynamic compression portion) between the head 6 and the threads 12. The central zone may provide spring like geometry that enhances the elastic behavior. The central zone 28 also uses an elastic material (e.g., Nitinol) rather than titanium or stainless steel. Nitinol has a Yield Point (stress/strain point resulting in permanent deformation) at approximately 40 times greater strain than that of the titanium and stainless steel. The Nitinol may be particularly useful for its properties of elasticity, strength, and biocompatibility, rather than as a thermal controlled shape memory material; the thermal shape memory function does not need to be utilized for this purpose. The central zone 28 may be configured to have a first axially compact configuration central zone 28 and a second axially elongated configuration central zone 28', and the central zone 28 may transform smoothly or continuously between these configurations. In some examples, the central zone 28 may be placed into the second, axially elongated configuration as the implantable device is screwed into a bone channel. FIG. 2C shows the implantable device 22' in place in a broken bone 102. The implantable device 22 can be screwed into pre-drilled bone channels of a broken bone to be joined together with compression. As the implantable device 22 is screwed into place in the broken bone 102, the distal helically threaded zone with threads 12 at the distal end 20 are positioned across the break (joint) 112 entirely into the second bone segment 106 on the distal or far side bone. As the implantable device 22 is further advanced/screwed in, the proximal head 4 will engage the first bone segment 16 on the near side. Further rotation of the screw will pull the far side against the near side of the joint compressing the joint. The compression force increases with further rotation until the plateau stress level in the central zone of the Nitinol device is reached, and from that point on, further rotation of the implantable device 22 will result in approximately constant compression of the joint up to about 6% of the length of the central zone 28. This compression range (6% plus typical for NiTi I SE 508 SR) and the "close to constant" force attributes of the Nitinol plateau strain behavior allow a large degree of latitude for the surgeon to bring the bone joint segments together, apply a compression level (which may be pre-determined), and to accommodate the immediate joint resorption while maintaining compression over time. Devices made from titanium or stainless steel seldom can retain any compression on a joint even for a short time after insertion since resorption of the bone surfaces in compression is often greater than the small compression motion the 0.2% strain yield point of these materials provides. The central zone 28 may be lengthened (deformed) into the second, axially elongated configuration. The central zone 28 may also be lengthened into the second, axially elongated configuration and held. In some variations, the central zone 28 may be cannulated (tubular/hollow). In some other variations, the central zone is non-cannulated (solid).

In order to axially extend and/or axially contract, the central zone of an implantable compression screw as described herein may be configured to move (e.g., glide or slide) through a bone channel through which it is inserted. For example, the central zone may be relatively smooth (unthreaded), although the distal end may be threaded. The central zone may lack other features (e.g., anchor tabs) that may be present at the distal end of the implantable device for anchoring the implant relative to a bone channel. The central zone 28 may be a suitable length for a specific joint size and depth into a bone. A head 4 of a screw may have a mating part 6 for mating with a screwdriver (e.g., a hexagonal, Allen, torq, slotted, cruciate, or Phillips head screwdriver; not shown). FIG. 2B shows a comparison of material properties for an implantable device 22 (made of Nitinol) as described herein and another typical bone (such as a cortical bone). FIG. 2B shows a stress-strain graph of force vs. % elongation. The curve for the titanium screw shown in FIG. 1A is shown at the left for reference. When inserted at a stress below the yield point, the implantable device 22 can exert compressive stress on the broken bone as the bone is compressed or pulled towards its original size and shape. However, if the implantable device 22 is stretched beyond the yield point, the implantable device 22 shows permanent strain deformation (plastic behavior); it has been stretched too far and cannot return to its original size. Thus, beyond this point it cannot exert a desired compressive force on the healing bone. The device curve closely matches the human bone curve over a range of motion of greater that 3% at close to constant force. Further rotation/screwing-in of the device does not increase the compression level and provides a total range of motion over 6% to accommodate resorption and any alignment associated motion as well.

Figure 3A:
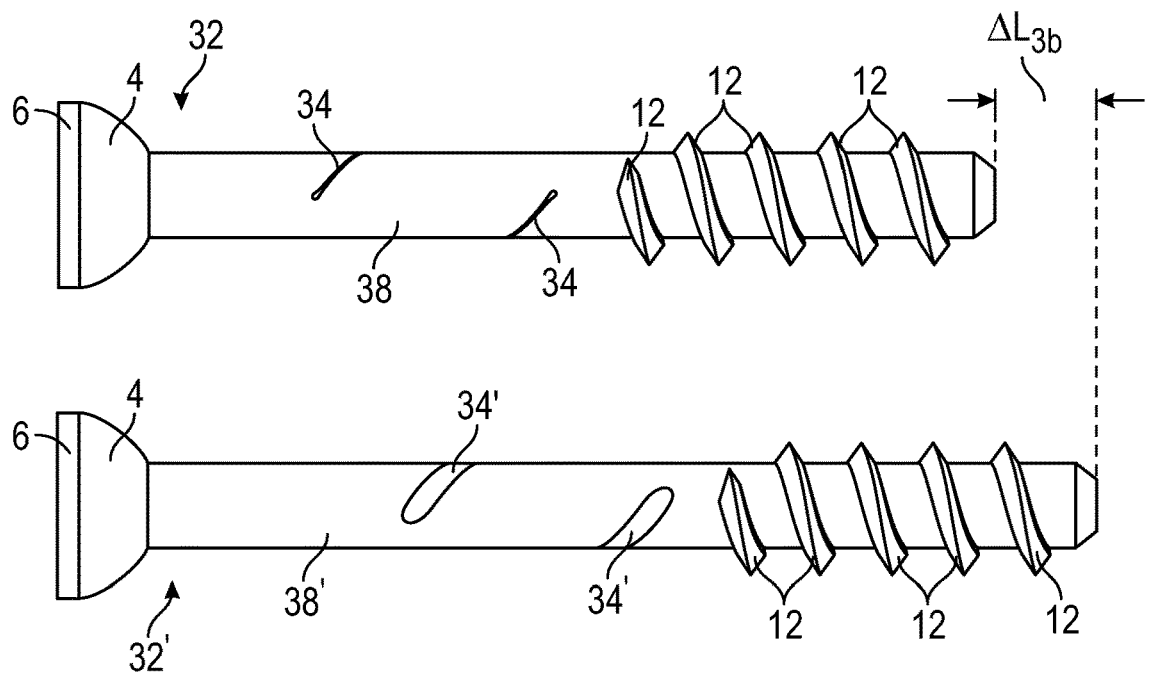
FIG. 3A shows two configurations of implantable device with a helical region for dynamic compression and improved material properties.

Also described herein are implants that include a feature, such as a geometrical or mechanical feature, and the feature may control (at least in part) feature elasticity, feature compression, and/or feature length. The feature may be in a central zone of an implant and changes to the feature may control and change device elasticity, device compression, and/or device length. In some examples, a feature may be a helical region or part of a helical region in the central zone of an implantable device. A feature, such as a helix (as used herein, a helix also includes a spiral and variations) may have spring or spring-like properties. A central zone (or an entire implant) may be made from a material that itself has good elastic characteristics (e.g., greater than the elasticity of stainless steel or titanium implant material), such as Nitinol. The central zone having the feature may be cannulated (hollow) or non-cannulated (e.g., a solid rod). FIG. 3A shows an example of an implantable device 32 (a dynamic compression screw) in an unstressed state. Similar as to described above for the implantable device 22, implantable device 32 has head region 4 at the proximal end and a distal helically threaded zone with threads 12 at the distal end 20. Implantable device 32 has a central zone 38 between the head region 6 and the threads 12, and the central zone 38 includes a helix 34. Similar as to described above for the implantable device 22, the implantable device 32 can be inserted into a bone using a screwdriver that mates with mating part 6 at the proximal end. The head region 4 can hold the proximal end of the implantable device 32 on the proximal end of a first bone segment, the threads 12 can anchor the implantable device 32 into a second bone segment on a distal end, and the central zone 38 can cross a break in the bone. Rotating/screwing implantable device 32 further into the bone, the break in the bone can be reduced, and the proximal segment and distal segment of the bone can be pulled closer together. As shown in the bottom of FIG. 3A, rotating/screwing implantable device 32 into the bone, elongates helix 34', the central zone 38', and implantable device 32' by a length represented by ΔL3b. The helix 34/34' may be configured to axially elongate and axially contract, increasing and decreasing the length of the central zone 38/38' and the implantable device 32/32'. The helix 34/34' may be configured to axially elongate and axially contract in response to applied force and may do so continuously rather than "snapping" from the top configuration to the bottom configuration. Once elongated, the elongated helix 34' can provide compressive force over the bone segments during bone healing (e.g., for 0-8 weeks such as for normal bone healing, or longer (e.g., for 8 weeks—2 years, or longer for abnormal bone healing or additional bone remodeling).

Figure 3B:
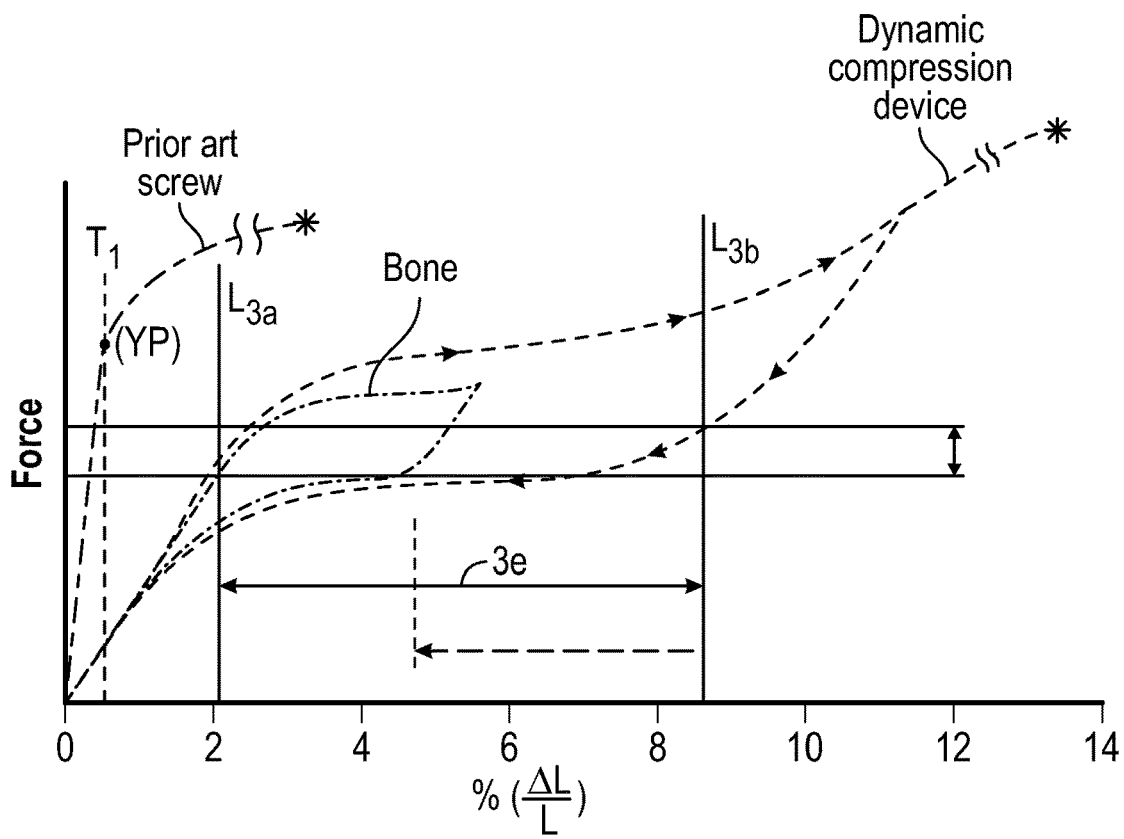
FIG. 3B shows a stress-strain graph showing the overlap in material properties of the device shown in FIG. 3A with properties of a typical bone.

FIG. 3B shows a stress-strain graph of elastic properties of the implantable device 32/32' shown in FIG. 3A. The graph of elastic properties in FIG. 3B shows the effect of adding a helical cut to the central length of a Nitinol device (such as the one shown in FIG. 2A), creating a spring like elastic action in this zone as the helical cut is stretched and released (see the dotted line with right pointing and left pointing arrowheads showing, respectively, elastic stretch and elastic recovery). FIG. 3B shows that a total range of motion for the implantable device 32/32' can be greater than 12%, with no permanent strain. The elastic action can be controlled by various parameters (e.g., adjusting the pitch or number of turns of the spiral per unit length) and the wall thickness of tubular body of the device. FIG. 3B also shows that matching implant properties to bone properties with constant compression forces, greater than a 3% range of motion is achieved. This range of compressive motion is greatly increased over the range compared to the prior art screw shown on the left side of the figure and in FIG. 1B. FIG. 3B also shows the implant range of axial motion or working compression e (between L1 and L2) is from about 2% to about 8.5% elongation/contraction. FIG. 3B also shows the degree f of implant contraction upon implantation due to resorption upon release. A feature may be a helix and/or a spiral extending or wrapping around a longitudinal axis of an implantable device or may be another geometrical/mechanical feature or form (e.g., a series of holes or slits) that improves elasticity especially in the central zone of an implant. A helix may be generally circular (e.g., have a generally constant radius or constant curvature). A spiral may include winding in continuous and gradually widening or tightening manner, such as in a curve around a longitudinal axis of the implant. A helix or spiral may be regular or irregular. A helix or spiral may be curved, bulging, flattened, or rounded. In some variations, a helix or spiral may be circular, ovoid, triangular, saddled, or square. A feature, such as a helix or spiral, may be made using a laser cut into a rod or by winding and shaping a wire to the desired shape. Various parameters of a feature, such as a helix wall thickness of an elastic (e.g., Nitinol) tube in the central elastic zone, the pitch of the helix, the number of turns of the helical cut per unit length, and/or the number of helices control enable the elastic behavior of the device. The device can be pre-designed allowing control of range of motion and absolute compression forces of the device. A thicker tube wall can result in higher absolute forces, while retaining the range of motion. Higher pitch (turns/length) can result in larger range of motion at the expense of absolute forces. A wall thickness of a helix can be greater than 0.1 mm, greater than 0.5 mm, greater than 1 mm, greater than 2 mm, greater than 5 mm or less than 5 mm, less than 2 mm, less than 1 mm, less than 0.5 mm or and values between these. A wall thickness can extend all the way to an implant hollow interior or can extend partway. A pitch of a helix can be a desired size such as greater than 0.1 mm, greater than 0.5 mm, greater than 1 mm, greater than 2 mm, greater than 5 mm or less than 5 mm, less than 2 mm, less than 1 mm, less than 0.5 mm or and values between these. A feature, such as a helix, can have at least one turn, at least two turns, at least three turns, at least four turns, at least five turns or at least ten turns, or not more than ten turns, not more than five turns, not more than four turns, not more than three turns, not more than two turns or one turn or fewer than one turn or values between these (e.g., at least one turn and not more than six turns). Although the number of helical turns, can be an integer (1, 2, 3, etc.) the number of turns can also be fractional (e.g., two and a half turns). In some variations, a feature (a helix) may be a partial helix (e.g., half of a helix). An implant may include one helical feature (one helix) or more than one helix. For example, two helices could be wrapped around a single length of a central zone, or two helices could be placed longitudinally adjacent to each other. This added geometry to the elastic central zone of the device allows the range of motion to be extended from about 6% (for a Nitinol central zone without this geometry) to beyond 15% (for a Nitinol central zone with this geometry), thus giving a surgeon more latitude for adjustment and less sensitivity to particular positioning of the device. The flexibility of the device introduced by the feature or helix also contributes to more fatigue failure resistance since small deflections are accommodated and recovered. A subset of any different implant features or parameters listed herein can be combined and may be particular suited to a certain bones or groups of bones (e.g., thigh bone (femur), kneecap (patella), shin bone (tibia), fibula, shoulder blade (scapula), collar bone (clavicle), humerus, radius, ulna, cervical, thoracic vertebrae, lumbar vertebrae, sacrum, tailbone (coccyx), skull, jawbone, ribs, breastbone (sternum), wrist bones (carpals), metacarpals and phalanges. In some variations, part of an implant as described herein may cross an intervening structure, such as a bone plate and may hold the intervening structure in place, against a bone.

Figure 4A:
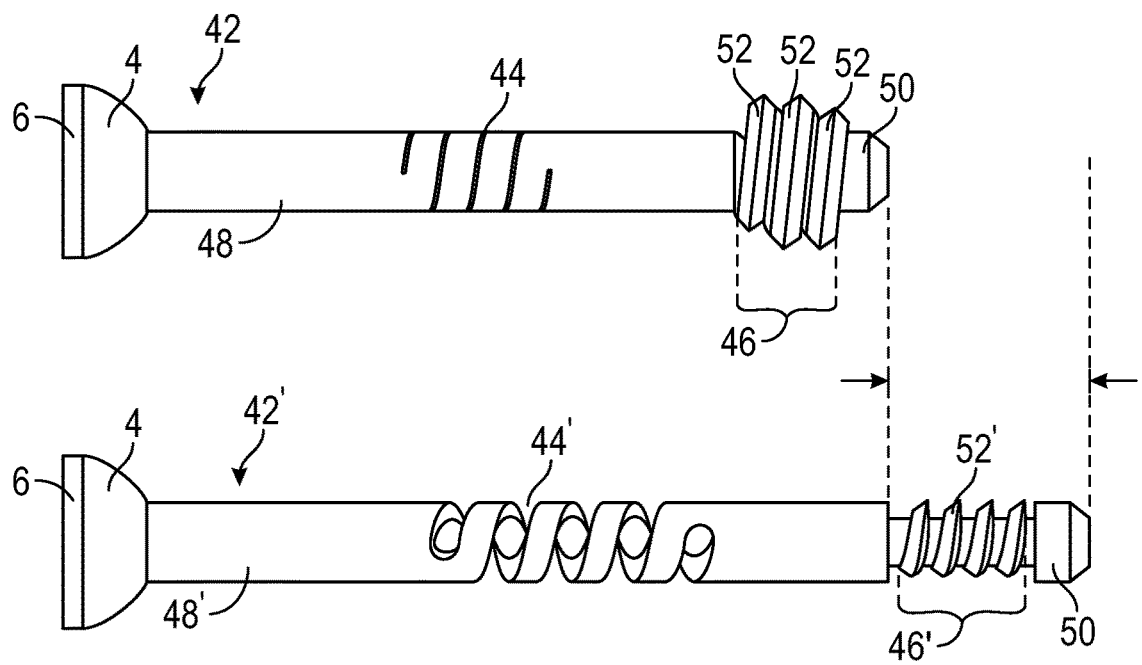
FIG. 4A shows two configurations of implantable device made from Nitinol with a proximal helical region for dynamic compression and a compressible distal threaded region.
Figure 4B:
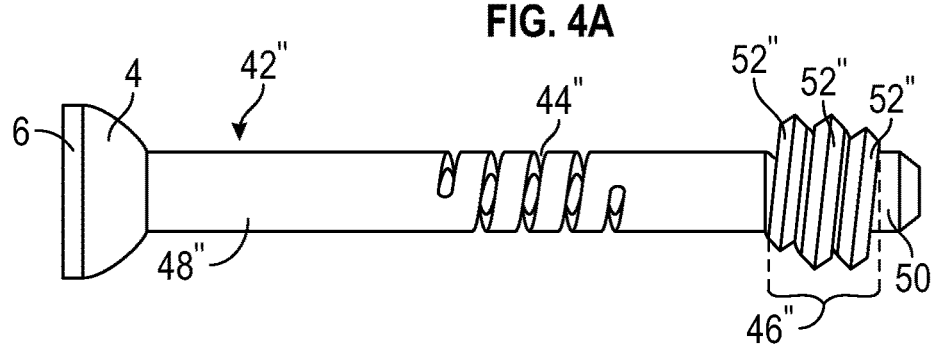
FIG. 4B shows the implantable device shown in FIG. 4A after implantation.

Also described herein are implantable devices requiring zero insertion force (ZIF). These implantable devices are inserted, in part using a shape memory material and do not require torque, rotation, or tapping for insertion into a broken bone. The implantable devices may have a distal anchor feature that can transform from a radially compressed shape (e.g., a deformed, shape memory shape) for insertion to a radially expanded shape for anchoring the implant in a bone channel. The distal anchor feature may be a helical coil zone and may have a thread geometry in the Nitinol tube distal end that resembles a typical thread geometry. They may be inserted by a different mechanism from that of a typical threaded distal end. FIG. 4A shows an example of an implantable device 42 requiring zero insertion force for inserting into a bone. The implantable device 42 at the top of FIG. 4A shows the device as manufactured from NiTinol before deformation. The implantable device 42 is similar to the implantable device 32 shown in FIG. 3A, except that the distal threaded region 12 in the implantable device 32 shown in FIG. 3A is replaced with an anchor 46 at the distal end 50 of the implantable device 42. The anchor 46 is provided as a helical coil zone resembling a typical thread geometry in the Nitinol tube distal end. Similar to as described above for FIG. 3A, the implantable device 42 may be made of an elastic material, such as Nitinol. However, here the anchor 46 may be "shape set" using Nitinol shape setting techniques. FIG. 4A also shows the implantable device 42' deformed, and axially pre-stretched by about 6% as shown by the double dotted lines comparing the length of the deformed implantable device 42' with the implantable device 42 as manufactured. The implantable device 42' is ready for insertion in a pre-drilled hole in a bone needing fixation. The anchor 46 can be diametrically expanded to anchor 46' as shown in FIG. 4A (e.g., at least 1.1× its original diameter, at least 1.5× its original diameter, at least 2.0× its original diameter, at least 2.5× its original diameter, or not more than 2.5× its original diameter, not more than 2.0× its original diameter not more than 1.5× its original diameter or any value between these amounts (e.g., at least 1.5× and not more than 2.3× its original diameter)). For insertion into a bone channel in a bone, expanded anchor 46 of the implantable device 42 shown in the top of FIG. 4A is compressed back to its original anchor 46' size, using an insertion tool (not shown in this view), such as a coaxial installer configured to extend inside a hollow implantable device 42. The insertion tool retains the anchor 46' of the implantable device 42' in the compressed state ready for installation in a pre-drilled bone channel. The insertion tool also axially stretches the implantable device 42' (e.g., the central zone 44') prior to insertion of the implantable device 42' into a bone channel. In some examples, a first bone segment is separated from a second bone segment by a bone break, and a first channel is made through the first bone segment and a second channel is made at least partially through the second bone segment, such as by drilling with a bone drill. The implantable device 42' can be inserted into a bone using the insertion tool. The implantable device 42' can be inserted through the first channel, across the bone break, and into the second channel to a desired depth. The head region 4 keeps the proximal end of the implantable device 42' on the proximal end of the first bone segment. The insertion tool is actuated, releasing the diametrically compressed anchor 46' at the distal end. FIG. 4B shows the implantable device 42' as recovered upon release from the insertion tool. The anchor 4 has transformed to a screw-like shaped anchor 46" and the axial pre-stretch in length has also mostly recovered. The diametrically compressed anchor 46 expands into the bone (e.g., bone surrounding the second bone channel) like a screw. The accessory tool is withdrawn from the implantable device 42" releasing the axial pre-stretched central zone 48' which shortens to central zone 44" (as seen in FIG. 4B), compressing the joint (break). The joint may be compressed to a pre-designed compression level. The central zone 48" may axially shorten (relative to the insertion configuration shown in the bottom of FIG. 4A). The joint may be compressed to a pre-designed compression level. The central zone 48" (and the helix 44") are elongated relative to the starting configuration of the central zone 48 (and the helix 44) shown in the implantable device 42 at the top of FIG. 4A. This double Nitinol super elastic recovery action will both anchor the anchor 46" in the distal bone segment and compress the distal segment and proximal segment axially together with a wide range of motion to accommodate resorption, initial compression of the joint, and continuing compression over time to enhance regrowth and strength of the repair site.

If further compression is desired, the implantable device 42" can be rotated/further inserted like a screw, such as by mating a screwdriver with mating part 6 on the proximal end of the implantable device and rotating the implantable device 42" (e.g., rotating clockwise). The head region 4 can hold the proximal end of the implantable device 42" on the proximal end of a first bone segment and the implantable device 42" can be rotated so that threads 52" rotate and extend further distally, elongating the device between the head region 4 and the threads 52". In this way, the break in the bone can be further reduced, and the proximal segment and distal segment of the bone can be pulled closer together. Opposite rotation (e.g., counter-clockwise) of the screwdriver results in relaxing the compression of the implantable device 42". Continuing rotation (e.g., counter-clockwise rotation) allows removal of the device.

Figure 4C:
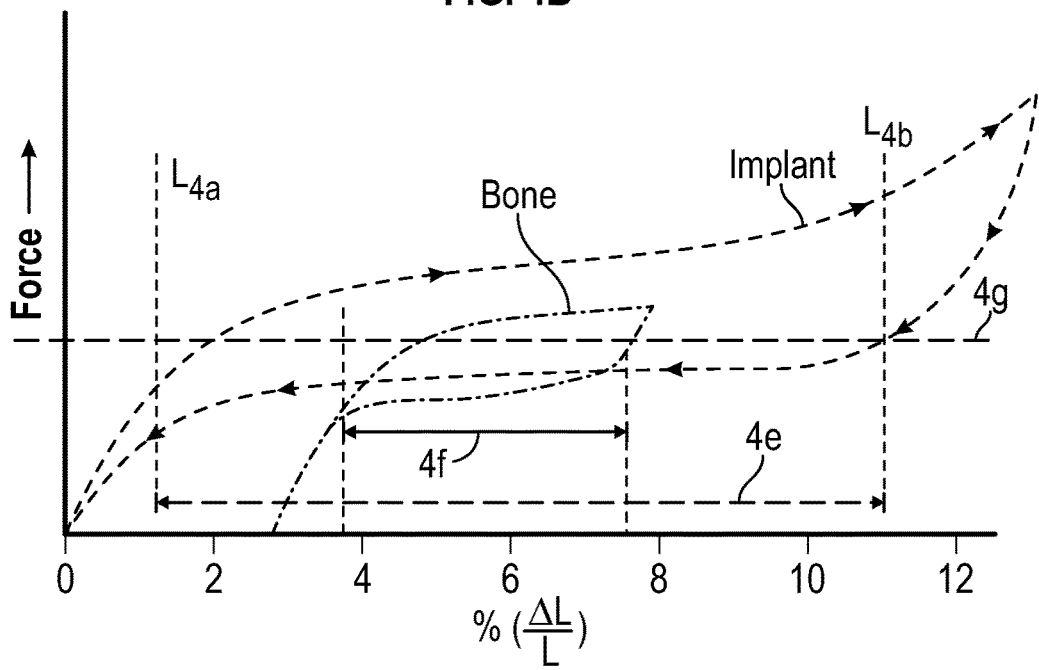
FIG. 4C shows a stress-strain graph showing the overlap in material properties of the device shown in FIGS. 4A-4B with properties of a typical bone.

FIG. 4C shows a stress-strain graph based on the implantable device 42 shown in FIG. 4B and FIG. B. The graph of clastic properties in FIG. 4C shows the effect of adding a deformable anchor 46 (as well as the helical cut 44 to the central zone 48) of a Nitinol device creating a spring like clastic action as both the deformable anchor 46 and helical cut 44 stretched and released (see the dotted line with right pointing and left pointing arrowheads showing, respectively, clastic stretch and elastic recovery). The dynamic compression working range 4c (between L4a and L4b) extends over 10%. As shown in arrow 4f in FIG. 4C, matching implant properties to bone properties with constant compression forces, greater than a 3.5% range of motion is achieved. The clastic match with human bone properties is shown. Installation of the implantable device into a bone requires no rotation or torque on the installer accessory and no tapping of the pre-drilled hole. The installed implantable device can be adjusted for position by rotation either in or out. The set-up also allows removal of the device if necessary, either immediately or later in time. As with any of the helical cut compression devices, the flexibility inherent with the helical cut shaft will improve fatigue failure resistance as well.

Figure 5A:
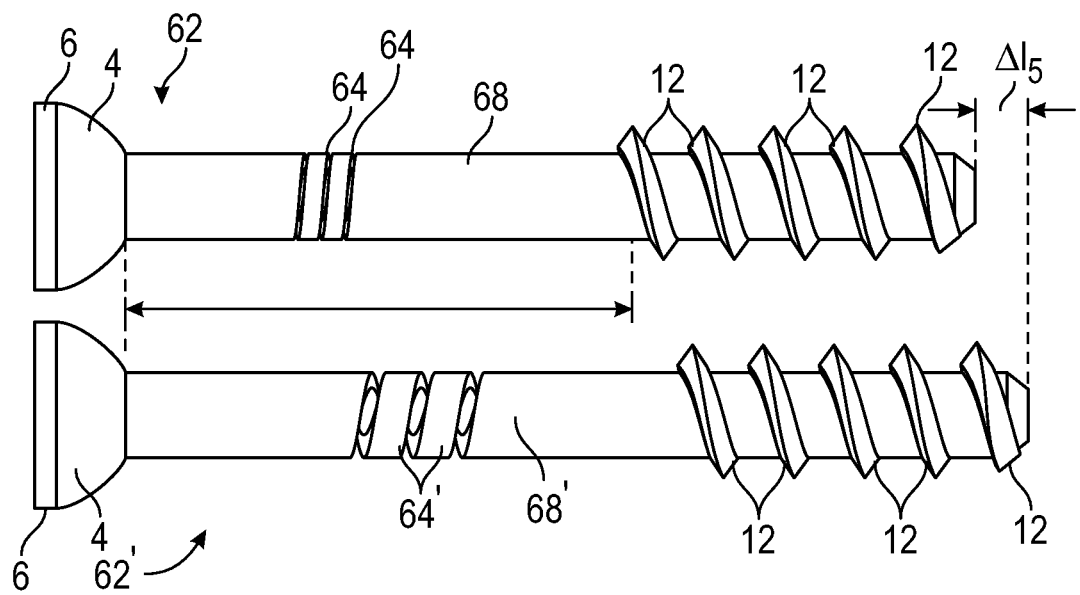
FIG. 5A shows two configurations of implantable device made from a titanium alloy or stainless steel with a proximal helical region for dynamic compression and a distal threaded region.

Also described herein are implantable non-Nitinol devices such as a cannulated titanium or stainless steel cannulated screw with a wide range of motion compression capability with the addition of a feature, such as a geometrical or mechanical feature, and the feature may control (at least in part) feature elasticity, feature compression, and/or feature length. The feature may be in a central zone of an implantable non-Nitinol device and different features may control and change device elasticity, device compression, and/or device length. In some examples, a feature may be a helical region or part of a helical region in the central zone of an implantable device. A feature, such as a helix (as used herein, a helix also includes a spiral and variations) may have spring or spring-like properties. A central zone (or an entire implant) may be made from a material that itself has limited range of compression (e.g., 0.2%), such as stainless steel or titanium implant material (e.g., ß Ti or Ti64 (Ti6Al-4V) alloy. The central zone having the feature may be cannulated (hollow) or non-cannulated (e.g., a solid rod). In some examples, a feature may be a helical region or part of a helical region in the central zone of an implantable device. FIG. 5A shows an implantable device 62 and implantable device 62'. The implantable devices 62/62' are similar to the implantable device 32 above except the implantable device 62 is not made from a substantially elastic material (e.g., Nitinol). The implantable device 62 is made from a substantially inelastic material, such as a titanium alloy or stainless steel. Titanium alloy or stainless steel devices on the market devices have a very limited compression range and virtually no matching or overlap of elastic properties with bone. Although the particulars of material properties of the titanium alloy or stainless steel of the implantable device 62/62' is different from the material properties of Nitinol of the implantable device 32/32', a wide range of motion compression capability with the addition of a feature both have a wide and useful range of motion compression capability.

Figure 5B:
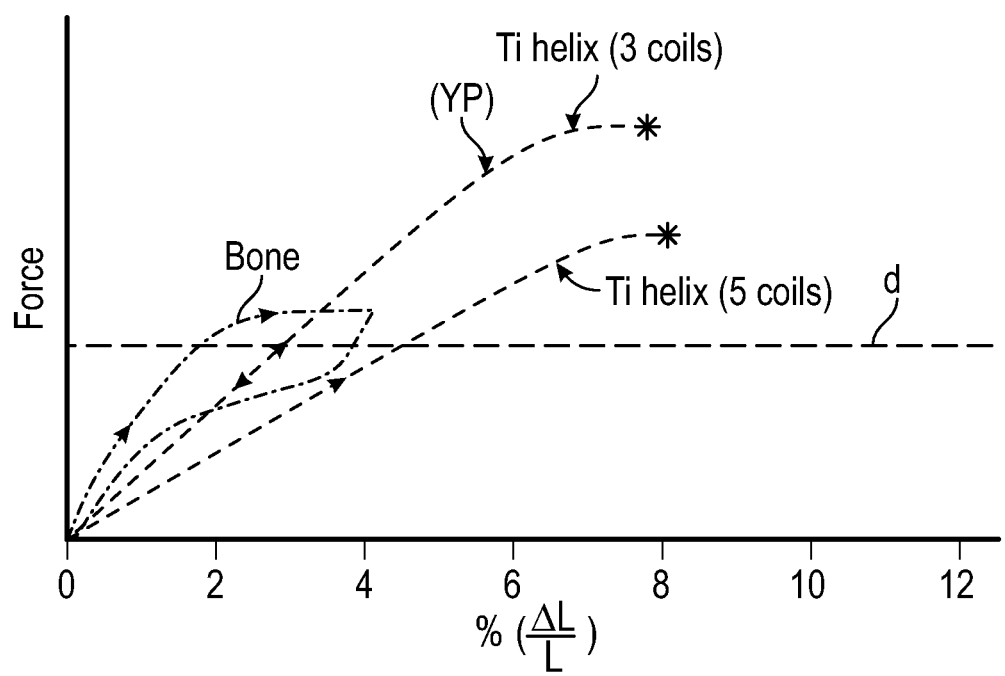
FIG. 5B shows a stress-strain graph showing the overlap in material properties of the device shown in FIG. 5A with properties of a typical bone.

FIG. 5B shows a stress-strain curve of the implantable device 62/62' shown in FIG. 5A with either 3 helical coils or 5 helical coils and a typical bone. FIG. 5B shows the desired compression level d. FIG. 5B also shows the yield point (YP) for an implantable device 62/62' of titanium with 3 helical coils. The yield point for an implantable device 62/62' of stainless steel with 3 helical coils is very similar. FIG. 5B illustrates the enhanced elastic effect of providing a helical cut pattern in the central zone of a titanium or stainless-steel device. The effect is to allow this device to acquire much enhanced elastic properties in compression range of motion. For example, from just 0.2% without the added helical cut to as much 6% or more total range of motion. Because titanium does not have the super elastic hysteresis behavior of Nitinol, this embodiment may not provide the constant force features of the devices of FIGS. 2A, 3A, and 4A. It also may not have as much of a range of motion, but it does offer significantly improved performance due to the matching bone characteristics.

FIG. 6A shows different sizes of an implantable device 72' with an expanded helical region 44' and ready for use. These may be used for different types of bones or different types of injuries. The different sizes could be available in a kit for surgical use. The implantable device 72 is similar to the implantable device 32 except instead of threads on the distal end, the implantable device 72 has an anchor 76 including a plurality of tabs. The tabs can be in a compact configuration during insertion through the first bone segment and the second bone segment and take on an expanded configuration in the second bone segment. In some variations, the tabs are shape memory (e.g., Nitinol).

Also described herein is an insertion tool for inserting and installing an implantable device into a bone or other substrate. The insertion tool can hold the implantable device in a first, contracted configuration for insertion and then convert the implantable device to a second, expanded configuration. FIG. 6B and FIG. 6C show two enlarged fragmentary views showing the distal anchor region of one of the devices from FIG. 6A, shown first with the anchor 76 being held in a retracted state by the insertion tool 78 and then in a deployed state with the tool removed (FIG. 6C). The insertion tool and the implantable device may have mating parts (e.g., lock and key) or a frangible coupling between them. The insertion tool 78 can hold the implantable device 72 and anchor 76 in a first, contracted configuration (with the mating parts or frangible coupling) for insertion into a bone channel. The implantable device 72 and anchor 76 a second, expanded configuration shown in FIG. 6C. In some examples, inserting an implantable device into a bone or other substrate includes holding, with an insertion tool, the implantable device in a first, contracted configuration for insertion, inserting the implantable device through a bone, activating the insertion device to convert the implantable device to a second, expanded configuration.

FIG. 6D shows different sizes of the implantable device 42 that could be used for different types of bones or different types of injuries. The different sizes could be available in a kit for surgical use. FIG. 6E and FIG. 6F are two enlarged fragmentary views showing the distal anchor region of one of the devices from FIG. 6C, shown first with helical threads in a retracted state (FIG. 6E) and then in a deployed state (FIG. 6F). The helical threads may be held in the retracted state with an insertion tool. Similar to as described above for FIG. 6B and FIG. 6C, some methods include the steps of holding, with an insertion tool, the implantable device in a first, contracted configuration for insertion, inserting the implantable device through a bone with the insertion tool, activating the insertion device to convert the implantable device to a second, expanded configuration, and releasing the implantable device from the insertion tool, and removing the insertion tool from the bone.

FIG. 7A shows different sizes of the implantable device 32' that could be used for different types of bones or different types of injuries. The different sizes could be available in a kit for surgical use. FIG. 7B shows different sizes of the implantable device 22' that could be used for different types of bones or different types of injuries. The different sizes could be available in a kit for surgical use. FIG. 7C shows different sizes of the implantable device 62' that could be used for different types of bones or different types of injuries. The different sizes could be available in a kit for surgical use. FIG. 7D shows an implantable device 90'. The implantable device 90' is similar to the implantable device 32' except the implantable device 90' has a longitudinal slot 92' or cutaway region in the central zone 98' instead of a helix 34'. The longitudinal slot 92' or cutaway region increases the elasticity of the central zone 98', better matching the material properties of the implantable device 90' with bone. In some variations, the implantable device 90' is made from Nitinol. In some variations, the implantable device 90' is made from stainless steel or a titanium alloy.

FIG. 8 shows another exemplary implantable device 120 constructed according to aspects of the present disclosure. Device 120, similar to previously described devices 32 and 62, includes a canulated rod 122 extending between a proximal head 124 and distal threads 126. The canulated rod 122 is provided with a double helix cut 128 through its walls (i.e., a pair of interdigitated helical cuts.) Each end of each helical cut 128 is provided with an end geometry 130 that is different from the middle portion of the helix 128. In this exemplary embodiment, each end geometry includes a curved portion 132, a straight portion 134 and a circular portion 136. Straight portion 134 generally aligns with the longitudinal axis of device 120, and curved portion 132 transitions the trajectory of helical cut 128 between its normal pitch to the direction of the straight portion 134. Circular portion 136 is provided at the end of straight portion 134 opposite from curved portion 132. The curved portion 132, straight portion 134 and circular portion 136 of each end portion 130 cooperate to dissipate stresses that may be concentrated at the ends of the helixes 128, thereby preventing potential device fracture or failure. FIG. 9 depicts implantable device 120 as being semi-transparent, revealing the helical cuts 128 and end geometries 130 located on the opposite side of the device. As shown, the two interdigitated cuts 128 mirror each other and are 180 degrees apart.

In this exemplary embodiment, curved portion 132 has a radius substantially the same as the outer radius of cannulated rod 122 (i.e., within 100%+5%.) In other embodiments, curved portion 132 has a radius that is between either 10%, 25%, 50% or 75% and 100% of the outer radius of cannulated rod 122. In other embodiments, curved portion 132 has a radius that is between either 500%, 400%, 300%, 200% or 150% and 100% of the outer radius of cannulated rod 122. In some embodiments, all of the curved portions 132 have the same radius. In other embodiments, the curved portions 132 can include different radiuses. In some embodiments, the radius can vary over the curved portion. In some embodiments, the curved portion can subtend an angle between about 105 and about 135 degrees, or between about 95 and about 170 degrees as projected onto the circumference of canulated rod 122. In some embodiments, the curved portion can subtend an angle between about 5 and about 60 degrees, or between about 1 and about 180 degrees as projected onto a transverse plane perpendicular to the central longitudinal axis of canulated rod 122. In some embodiments, the curved portion can subtend a width between about 10% and about 50%, or between about 5% and about 100% of the diameter of canulated rod 122 as projected onto a plane having the central longitudinal axis of canulated rod 122 in it.

In this exemplary embodiment, straight portion 134 is generally aligned with the longitudinal axis of canulated rod 122 (i.e., within a range of +2° of the axis.) In some embodiments, straight portion 134 falls within a range of +5°, +10°, +15° or +20° of the axis. In this exemplary embodiment, the length of straight portion 134 is about 40% of the outer diameter of canulated rod 122. In some embodiments, the length of straight portion 134 is between about 15% and about 100% of the outer diameter of canulated rod 122. In some embodiments, the length of straight portion 134 is between about 0% and about 200% of the outer diameter of canulated rod 122. In some embodiments, the straight portion may be omitted. In these embodiments, the end of curved portion 132 may extend generally parallel to the longitudinal axis of the device.

In this exemplary embodiment, circular portion 136 has a diameter of about 180% the width of helical cut 128 in an unexpanded state, and about 10% of the outside diameter of canulated rod 122. In some embodiments, circular portion 136 has a diameter between 100% and 600% the width of helical cut 128 in an unexpanded state, or between 5% and 30% of the outside diameter of cannulated rod 122. In some embodiments, circular portion 136 may be omitted.

In some embodiments, electrical discharge machining (EDM) is used to form helical cut 128. The EDM wire can pass through the central longitudinal axis and both wall thicknesses in order to cut both helixes 128 and their respective end geometries 130 at the same time. In some embodiments, a 0.005±0.001-inch diameter EDM wire is used. Helical cuts 128 are shown with exaggerated widths for clarity in the drawings herein. In some embodiments, a laser or other cutting process may be used to make one or more helix cuts 128.

Figure 12:
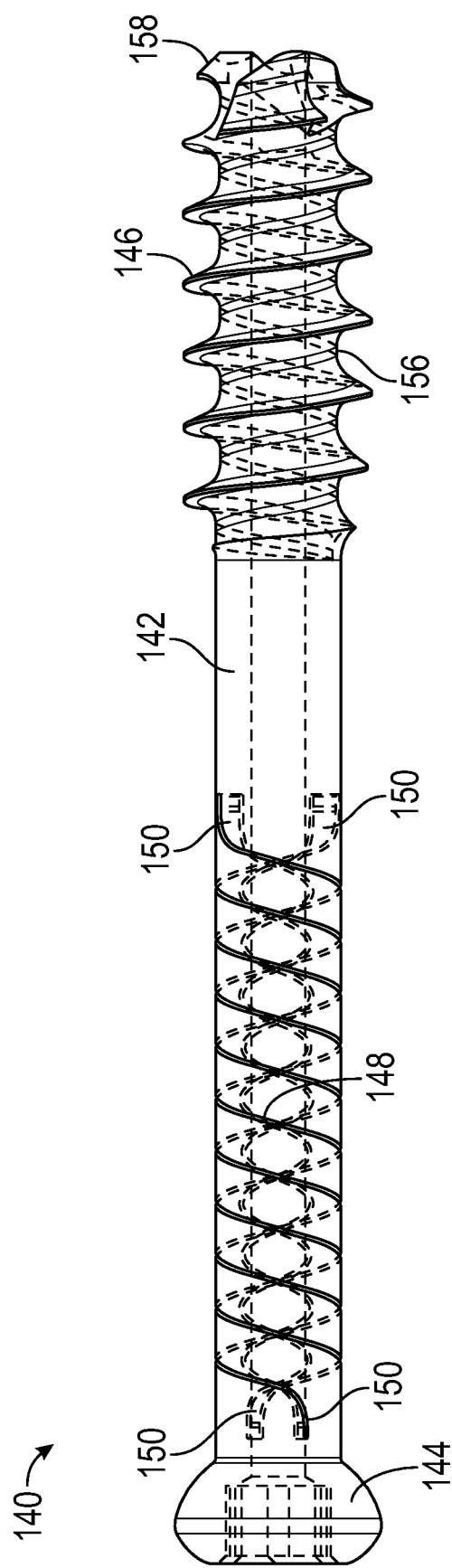
FIG. 12 shows a semi-transparent side view of the device from FIG. 10.

FIGS. 10-12 show another exemplary implantable device 140 constructed according to aspects of the present disclosure. Device 140, similar to previously described devices 32, 62 and 120 includes a canulated rod 142 extending between a proximal head 144 and distal threads 146. The canulated rod 142 is provided with a double helix cut 148 through its walls (i.e., a pair of interdigitated helical cuts.) Each end of each helical cut 148 is provided with an end geometry 150 that is different from the middle portion of the helix 148. In this exemplary embodiment, each end geometry includes a curved portion 152 and a straight portion 154. Straight portion 154 generally aligns with the longitudinal axis of device 140, and curved portion 152 transitions the trajectory of helical cut 148 between its normal pitch to the direction of the straight portion 154. The curved portion 152 and straight portion 154 of each end portion 150 cooperate to dissipate stresses that may be concentrated at the ends of the helixes 148, thereby preventing potential device fracture or failure.

FIG. 10 shows a side view of device 140 and FIG. 11 shows a perspective view. FIG. 12 is another side view but depicts implantable device 140 as being semi-transparent, revealing the helical cuts 148 and end geometries 150 located on the opposite side of the device. As shown, the two interdigitated cuts 148 mirror each other and are 180 degrees apart.

Device 140 is provided with another helical cut 156 located along the root of threads 146. This single helix cut allows threads 146 to expand, similar to threads 46 previously described relative to FIGS. 4A and 4B. Device 140 may be provided with internal sockets located at the proximal and distal ends and configured to receive mating insertion tools. By turning one socket relative to the other with the insertion tools, helical cuts 148 and 156 can be expanded. Alternatively, the insertion tools may be used to prevent the internal sockets from rotating relative to one another during insertion or removal of the device, thereby preventing helical cuts 148 and 156 from expanding or collapsing. Device 140 may also be provided with cutting features 158 on its distal end to allow device 140 to be self-boring and or self-tapping when being turned.

Figure 13:
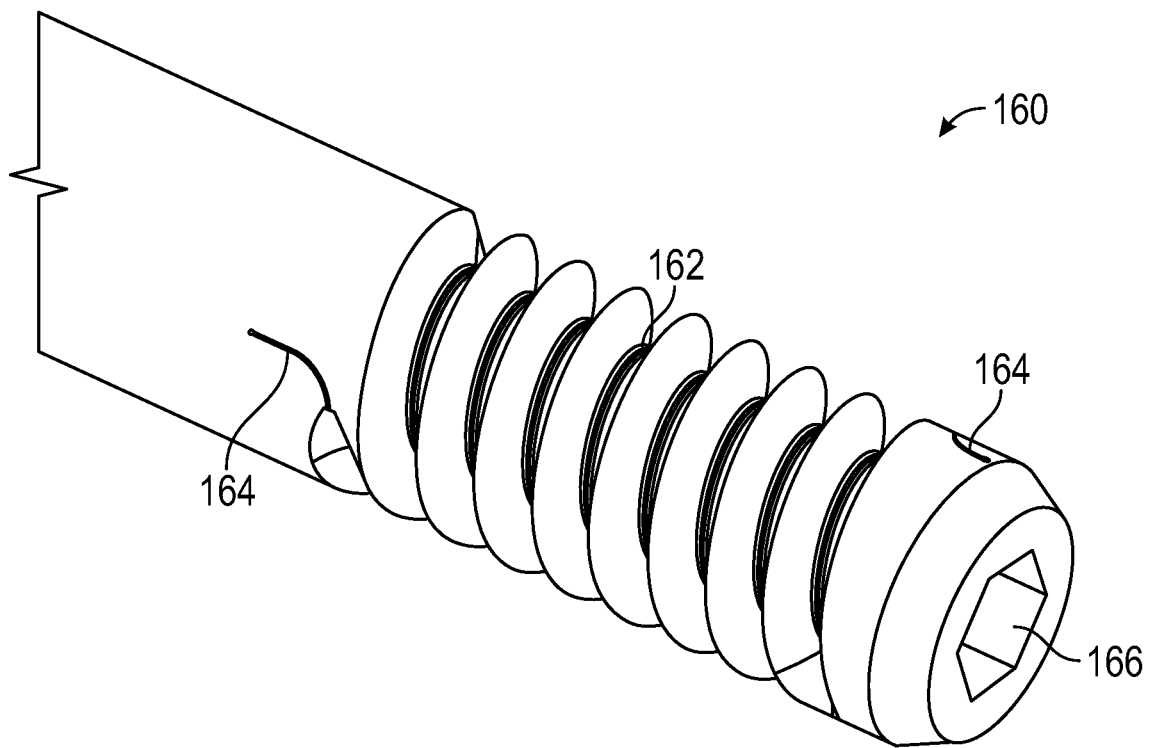
FIG. 13 shows another example of an implantable device having helix end geometries.
Figure 14:
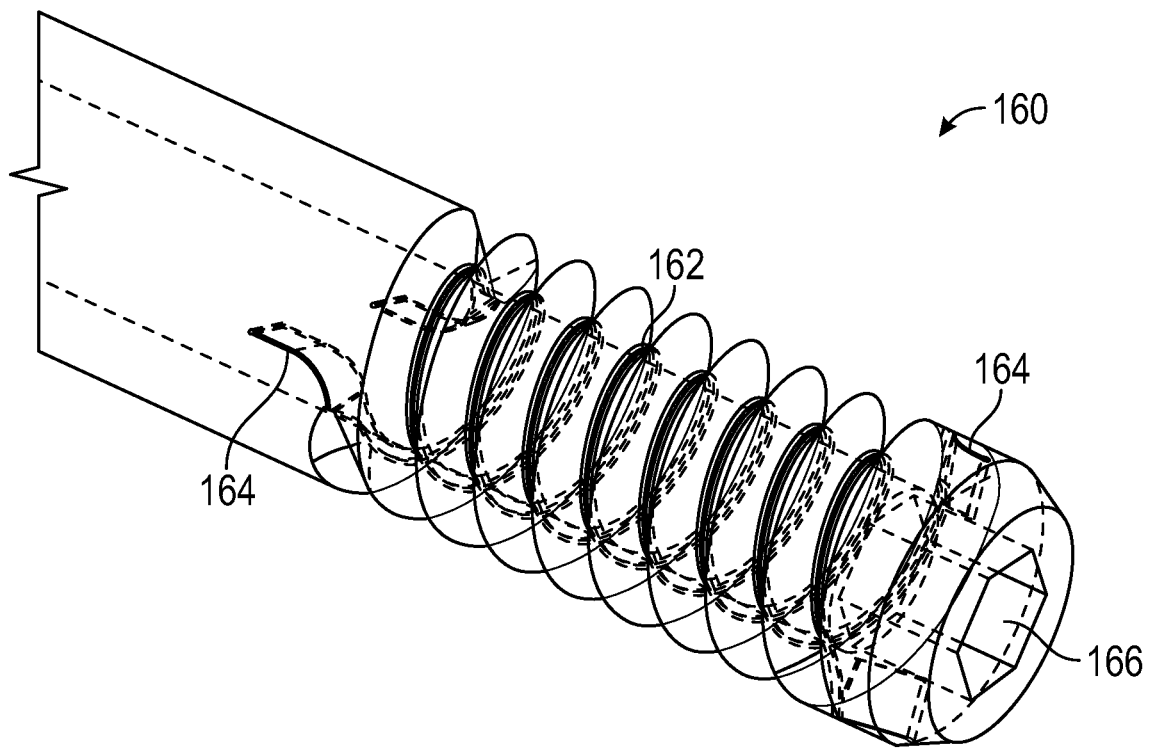
FIG. 14 shows a semi-transparent view of the device from FIG. 13.

FIGS. 13 and 14 show the distal end of another exemplary implantable device 160 constructed according to aspects of the present disclosure. FIG. 13 is an enlarged perspective view of the distal end of the device, and FIG. 14 is a similar view depicting the device as semi-transparent so that features on the opposite side and inside the device can be seen. Device 160 may be provided with a two-start set of threads, with an interdigitated pair of helical cuts 162 residing in the roots of the threads. Each end of each helical cut 162 is provided with an end geometry 164 that is different from the middle portion of the helix 162. In this exemplary embodiment, each end geometry includes a curved portion, a straight portion, and a circular portion, as previously described. Device 160 may also be provided with an internal socket 166 as shown for receiving the distal end of an insertion tool passing through the cannulated device. Socket 166 is shown as being hexagonally shaped. In other embodiments, the socket may be slotted, triangular, square, pentagonal, heptagonal, octagonal, star-shaped, oval, or other shape suitable for transmitting rotational forces from an insertion tool to the distal tip of the implantable device.

FIGS. 15 and 16 show another exemplary implantable device 170 constructed according to aspects of the present disclosure. FIG. 15 is a side view of device 170 and FIG. 16 is a cross-sectional side view. Device 170 is provided with a double helix cut 172 at the proximal end and a double helix cut 174 at the distal end, as previously described. Each end of each helix cut is provided with an end geometry that is different from the middle portion of the helix. An internal socket 176 is provided inside the proximal end and an internal socket 178 is provided inside the distal end. A circular or other shape cannula 179 runs through device 170 with a constant transverse cross-section so that a guidewire can be easily threaded through device 170 from either end. Tapered transitions may be provided between cannula 179 and sockets 176 and 178 to aid in the insertion of a guide wire.

Figure 17:
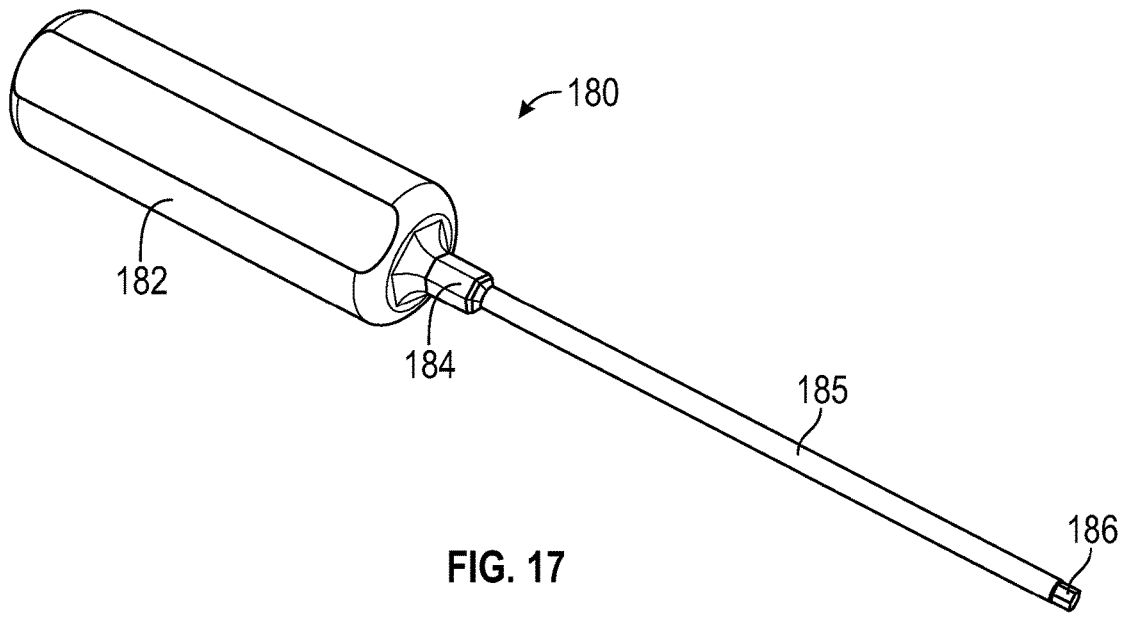
FIG. 17 shows an example of an insertion tool.
Figure 18:
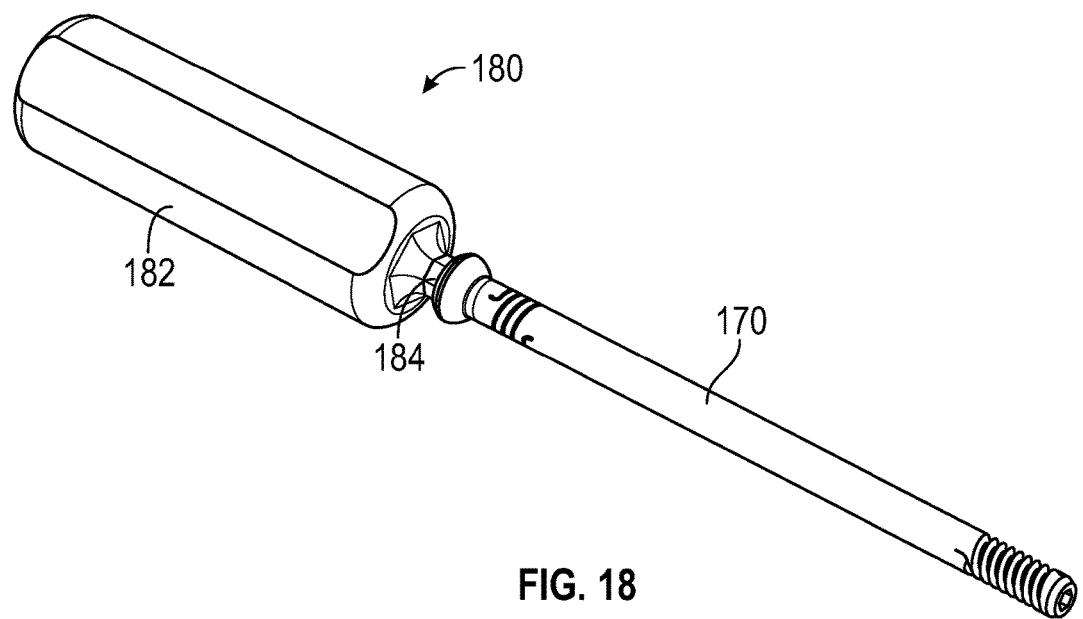
FIG. 18 shows the tool from FIG. 17 in use with an implantable device.

FIGS. 17 and 18 show an exemplary insertion tool 180 constructed according to aspects of the present disclosure. FIG. 17 is a perspective view of insertion tool 180 and FIG. 18 shows tool 180 inserted into implantable device 170 with device 170 shown as being semi-transparent. Tool 180 is provided with a handle 182, a proximal socket engagement portion 184 and a distal socket engagement portion 186. Distal socket engagement portion 186 is connected to handle 182 by an elongated shaft 185 configured to extend into the cannula of the implantable device. In some embodiments, socket engagement portions 184 and 186 are fixed relative to each other so that the helical cuts of implantable device 170 do not change their configuration when the device is being screwed into place. In other embodiment, socket engagement portions 184 and 186 may be rotated relative to one another so that the helical cuts of implantable device 170 may be opened and or closed before and or after device 170 is implanted. This may be accomplished by having two portions of handle 182 that can rotate relative to one another, each portion being connected to one of the socket engagement portions 184 and 186. With this arrangement, one handle portion may be held stationary while the other is rotated, such as to open up the helical cuts of implantable device 170. The two handle portions may then be releasably locked together to hold device 170 in this configuration until the handle portions are unlocked.

Figure 19:
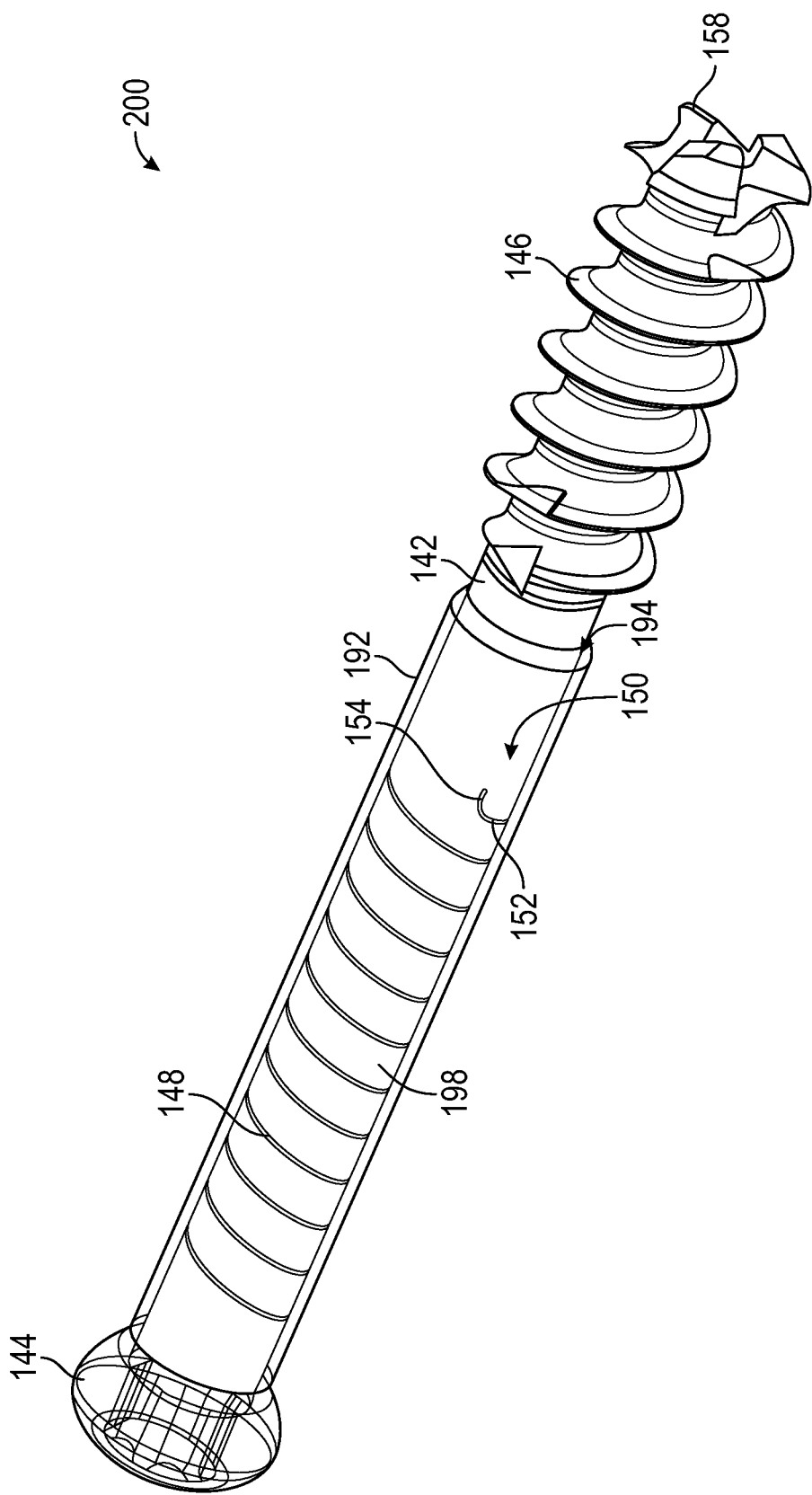
FIG. 19 shows an isometric view of an exemplary implantable device having a sleeve over a dynamically changeable helical region.

FIG. 19 shows an isometric view of another implantable device. FIG. 19 shows implantable device 200 with sleeve 192 over part of cannulated rod 142. FIG. 19 also shows proximal head 144 and distal threads 146 on the proximal and distal ends, respectively, of the implantable device 200. Sleeve 192 is illustrated in this view as semi-transparent in order to show sleeve 192 underlying helical cut 148 though the sleeve does not need to be and typically will not be semi-transparent. Sleeve 192 may advantageously provide support to cannulated rod 142 in a region(s) of cannulated rod 142 having dynamic compression portion 198 with helical cut 148, such as when dynamic compression portion with helical cut 148 radially expands. For example, dynamic compression portion with helical cut 148 may radially expand as implanted implantable device 200 is removed from a bone or other substrate. With some frequency, an implantable device, such as bone screws and devices such as described herein for orthopedic procedures, are placed in a patient and are left in the patient. In other cases, implantable devices, such as bone screws or the devices such as described herein, are placed in a patient and are subsequently removed from the patient. For example, it may be desirable to remove an implanted device from a patient because the patient has pain or an infection, especially pain or an infection at or near the surgical site. In other cases, it may be desirable to remove an implanted device because further surgery is required or because the implanted device interferes with joint movement. In some situations, removing an implantable device (e.g., implantable device 200) includes a step of rotating the implantable device in a removal direction and the removal direction may be opposite to an insertion direction. For example, for an implantable device rotated in a clockwise insertion direction, the device may be rotated in a counterclockwise removal direction. Rotating an implantable device in a removal direction may result in excessive torque developing in the implantable device. For example, a tight initial fit of an implantable device into bone, bone compression on the implantable device, bone realignment pressing the bone and implantable device together, or bone ingrowth into an implantable device can contribute to excessive torque developing in the implantable device during implantable device removal. In some situations, in which an implantable device is being removed, a dynamic compression portion of the device may not immediately return to an original shape. A dynamic compression portion may expand radially outward. For example, all or part of a dynamic compression portion (corresponding to one helical turn, two helical turns, at least half of the helical turns, etc.) may expand radially outward. An outwardly expanding dynamic compression portion may catch on, rub against, or compress against an inside wall in a bone hole and make implantable device removal difficult. According to aspects of the present disclosure, a sleeve over a dynamic compression portion can contain the dynamic compression portion in a desired or radially smaller size (relative to a maximum radially size). While sleeve 192 of implantable device 200 may contain a dynamic compression portion during device removal and limit or prevent radial (outward) dynamic compression portion expansion, it may be advantageous to minimize friction or gripping between an inside of sleeve 192 and an outside of dynamic compression portion during implantable device insertion into a bone or other substrate. During implantable device insertion into a bone or other substrate, the dynamic compression portion extends distally (e.g., relative to the sleeve, relative to the bone or substrate, or relative to a first implantable device configuration). FIG. 19 also shows gap 194 between an outside diameter of the dynamic compression portion and an inside diameter of sleeve 192. When implantable device 200 is in an initial or first axially compact configuration or in a second, axially elongated configuration (or in some situations during device removal), gap 194 may be present or a gap may not be present. Gap 194 may be relatively small. For example, in some embodiments, a gap between an outside diameter of the dynamic compression portion (or an outside diameter of the cannulated rod) and an inside diameter of sleeve may be no more than 0.001 of an inch, no more than 0.002 of an inch, no more than 0.003 of an inch, no more than 0.004 of an inch, no more than 0.005 of an inch, no more than 0.006 of an inch, no more than 0.007 of an inch, no more than 0.008 of an inch, no more than 0.009 of an inch, no more than 0.010 of an inch, no more than 0.015 of an inch, no more than 0.020 of an inch. For example, in some embodiments, a gap between an outside diameter of the dynamic compression portion (or a cannulated rod) and an inside diameter of sleeve may be at least 0.001 of an inch, at least 0.002 of an inch, at least 0.003 of an inch, at least 0.004 of an inch, at least 0.005 of an inch, at least 0.006 of an inch, at least 0.007 of an inch, at least 0.008 of an inch, at least 0.009 of an inch, at least 0.010 of an inch, at least 0.015 of an inch, or at least 0.020 of an inch. A gap between an outside diameter of the dynamic compression portion (or an outside diameter of a cannulated rod) and an inside diameter of a sleeve may be between any of these values such as at least 0.001 of an inch and no more than 0.010 of an inch. In some variations of an implantable device, an outside diameter of the dynamic compression portion and an inside diameter of the sleeve are in contact with one another. This may be the case during removal (or simulation of removal) of an implantable device from a substrate or bone or during implantation of an implantable device into a substrate or bone. In some variations, a dynamic compression portion and an inside diameter of a sleeve implantable device may be in contact prior to insertion or removal. For example, a dynamic compression portion and an inside diameter of a sleeve may be manufactured in contact with one another. The dynamic compression portion and an inside diameter of a sleeve may have a slip fit.

Similar as to other implantable devices as described herein, FIG. 19 also shows helical cut 148 has end geometry 150 that is different from the middle portion of the helix 148. In this example, end geometry 150 includes a curved portion 152 and a straight portion 154. Straight portion 154 generally aligns with the longitudinal axis of device 200, and curved portion 152 transitions the trajectory of helical cut 148 between its normal pitch to the direction of the straight portion 154. The curved portion 152 and straight portion 154 can dissipate stress that may be concentrated at the ends of helix 148, thereby preventing potential device fracture or failure. Although described with helical cut 148 and end geometry 150, implantable device 200, and any other implantable devices described herein, may have any features described herein, including but not limited to two or more than two helices, end geometry on a proximal end, end geometry on a distal end, end geometry on both the proximal end and the distal end, end geometry on neither end, etc. In some variations, an implantable device may have two or more than two discontinuous helices (e.g., helices that turn in the same general direction but which are not connected to one another). Each helix of the two or more discontinuous helices may independently have end geometry (such as end geometry 150) on a proximal end, end geometry on a distal end, end geometry on both proximal and distal ends, end geometry on neither end. In some variations, helical cut 148 can vary along its length in pitch, spacing of turns, etc.

Figure 20A:
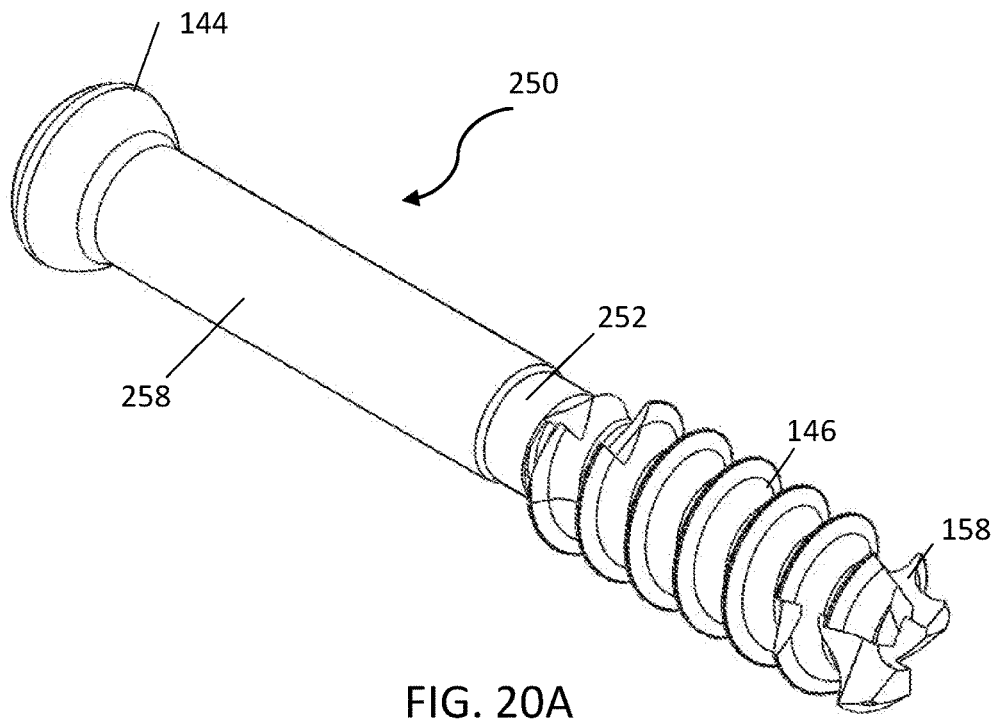
FIG. 20A-20D illustrate an exemplary implantable device with a sleeve and a method of assembling it. In this method, the sleeve precursor is initially attached to the head region and then the sleeve precursor with the attached head is placed over a cannulated rod.
Figure 20B:
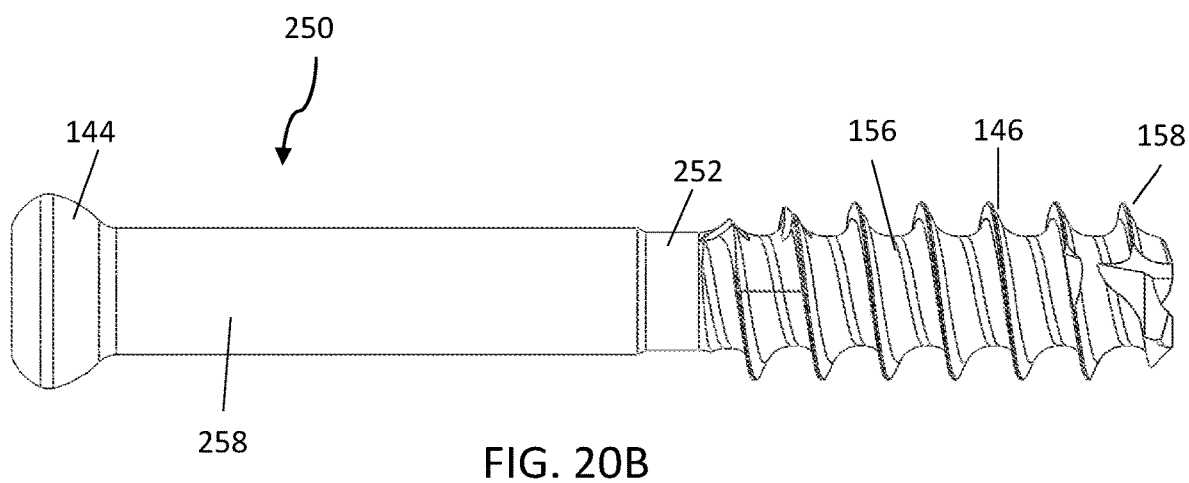

FIGS. 20A-20D illustrate another implantable device with a sleeve and a method of assembling it. In this method, the sleeve precursor is initially attached to the head region and the sleeve precursor and head are placed over a cannulated rod. FIG. 20A shows an isometric view and FIG. 20B shows a side view of implantable device 250 having sleeve 258 over a dynamic compression portion of cannulated rod 252.

Figure 20C:
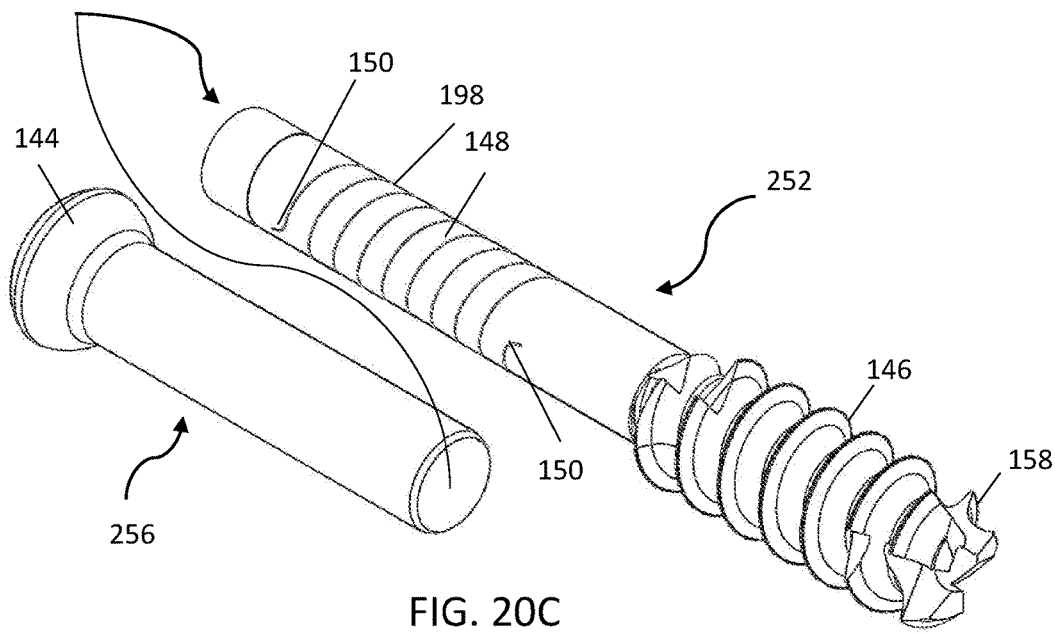
Figure 20D:
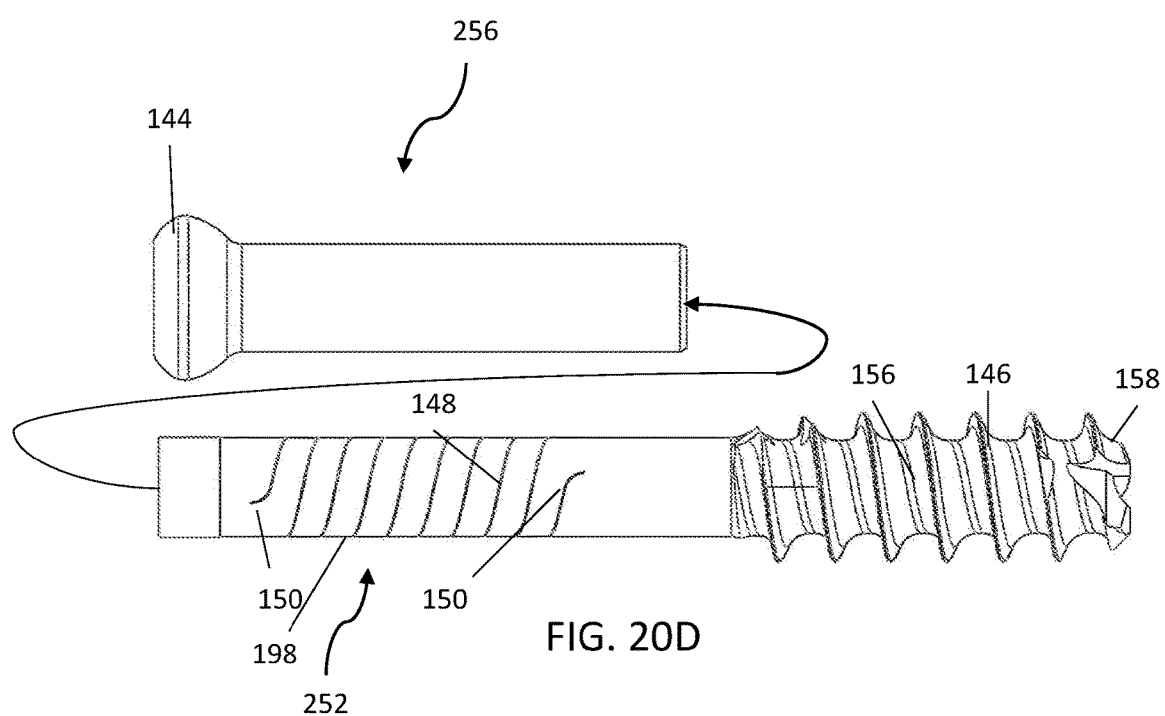
Figure 21:
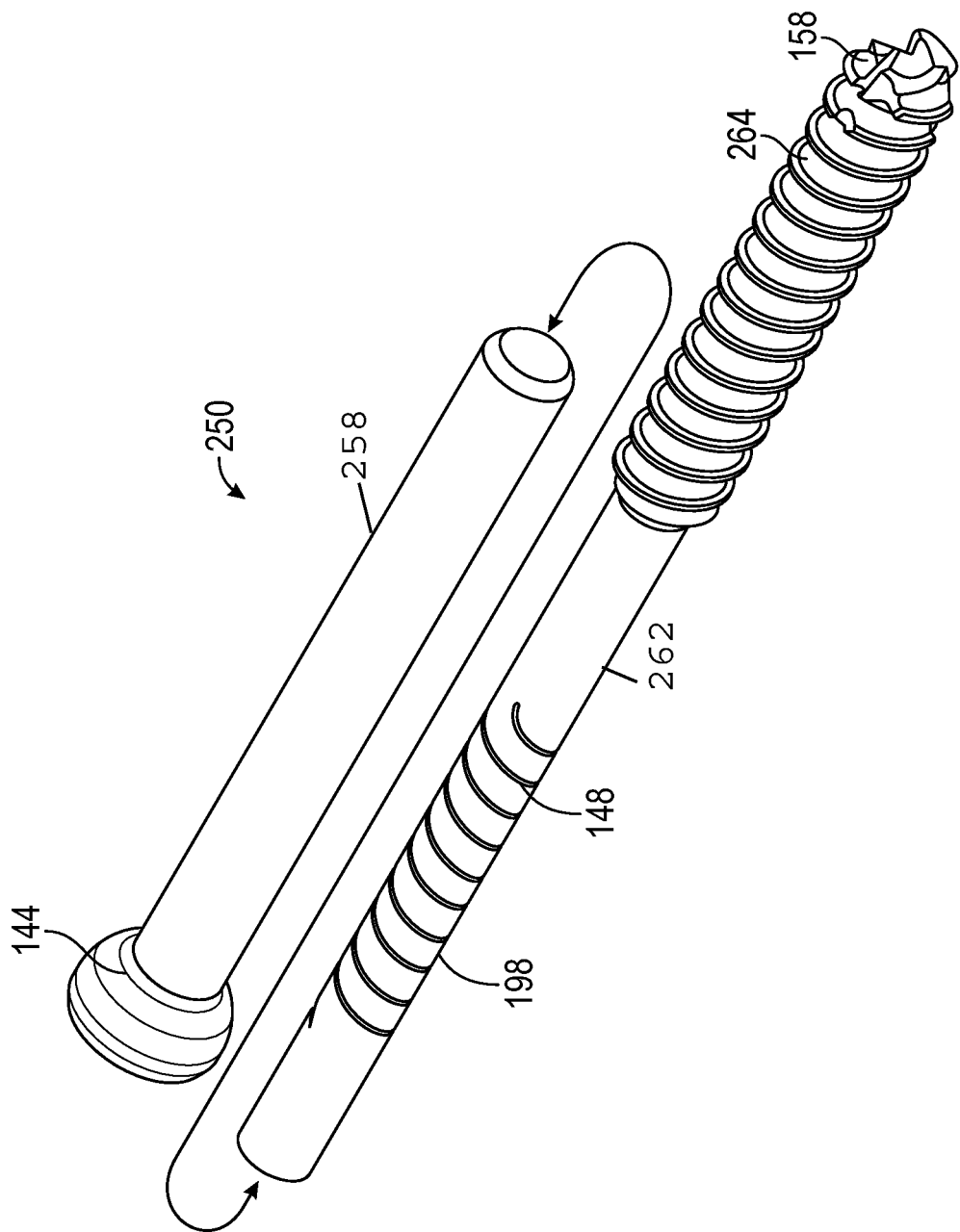
FIG. 21 shows an isometric view of a sleeve and longitudinal rod being assembled to form an implantable device having a sleeve over a dynamically changeable helical region. The sleeve and longitudinal rod are similar to those shown in FIG. 20A-20D except that the illustrated threaded end region contains more threads (single threads).

Head 144 and sleeve 258 are joined together. Cannulated rod is continuous with dynamic compression portion (under sleeve 258) and distal threads 146. Cannulated rod 252 has cutting feature 158 at a distal end. FIGS. 20A and 20B also show helical cut 156 in distal threads 146. FIG. 20C shows an isometric view and FIG. 20D shows a side view of sleeve 256 being placed over cannulated rod 252, as indicated by the arrows. Head 144 is positioned at proximal end of cannulated rod 252. FIG. 21 shows an isometric view of sleeve 258 and cannulated rod 262 being assembled to form implantable device 250 having sleeve 258 over dynamic compression portion 198. The sleeve and longitudinal rod are similar to those shown in FIG. 20A-20D except that distal thread 264 is illustrated with more helical turns (pattern of continuous elevations and depressions). A distal thread can have any number of helical turns. After placing a sleeve over a cannulated rod (or in other embodiments or variations), the head and/or the sleeve can be fastened to the cannulated rod. For example, a head can be fastened to a cannulated rod at a proximal cannulated rod end, a sleeve can be fastened to a cannulated rod at a cannulated rod proximal end, a cannulated rod middle portion, and/or a cannulated rod distal end. A head and/or sleeve can be fastened to the cannulated rod such as by adhering, bonding, gluing, or welding to adhere, bond, glue, or weld the different parts together. In this and other embodiments, a proximal end of a sleeve can be attached to a proximal end of the elongate body and/or a distal end of a sleeve can be attached to a distal end of the elongate body, such as by single piece manufacturing or by adhering, bonding, gluing, or welding to adhere, bond, glue, or weld the different parts together. In some variations, a proximal end of a sleeve is not attached to a proximal end of the elongate body. In some variations, a distal end of a sleeve is not attached to a distal end of the elongate body. In some variations, a sleeve is not attached to the elongate body. In some variations, a sleeve of an implantable device can slide over/along an elongate body and may do so during device placement and/or removal. In this and other embodiments herein, a sleeve and/or a portion of a sleeve can engender longitudinal motion relative to an elongate body and/or a portion of an elongate body. Any distal threads disclosed herein can have any number of helical turns; the additional helical turns here are shown for illustration purposes only. Any distal threads can have at least 1 turn, at least 2 turns, at least 3 turns, at least 4 turns, at least 5 turns, at least 6 turns, at least 7 turns, at least 8 turns, at least 9 turns, at least 10 turns, at least 20 turns, at least 30 turns, at least 40 turns, at least 50 turns, or at least 100 turns. Any distal threads can have at no more than 2 turns, no more than 3 turns, no more than 4 turns, no more than 5 turns, no more than 6 turns, no more than 7 turns, no more than 8 turns, no more than 9 turns, no more than 10 turns, no more than 20 turns, no more than 30 turns, no more than 40 turns, no more than 50 turns, or no more than 100 turns. Any distal threads can have a number of turns between these values (at least 1 turn and no more than 20 turns, etc.). In this and other embodiments of a sleeve or sleeve precursor, a sleeve or sleeve precursor may have a smooth inner surface or not have a smooth inner surface (e.g., may have a rough inner surface). In this and other embodiments of a sleeve or sleeve precursor, a sleeve or sleeve precursor may have a smooth outer surface or not have a smooth outer surface (e.g., may have a rough outer surface). In this and other embodiments, a sleeve is a single structure. In some variations, a sleeve may include more than one structure (such as two cuffs or tubes, three cuffs or tubes, etc.). In an implantable device, a sleeve will typically surround substantially an entire outside of a dynamic compression portion and/or an entire outside of a helical region. In this and some other embodiments of an implantable device, a head, a cannulated rod, a dynamic compression portion, and a bone engagement part are at least partially or are entirely made of a shape-memory material (such as nitinol). In some variations, at least a dynamic compression zone and a bone engagement part are made of a shape memory material. In some variations, a sleeve may be made of a metal (e.g., cobalt chrome nitinol, oxidized zirconium, stainless steel, titanium, titanium alloy), a medical grade polymer (e.g., polyaryl ether ketone (PAEK), polyether ether ketone (PEEK), polyetherimide (PEI), polyether ketone ketone (PEKK), poly phenylene oxide (PPO), poly phenylene sulfide (PPS), silicone, ultra-high molecular weight polyethylene (UHMWPE)), another material (e.g., bone, bone substitute material, carbon fiber, carbon fiber reinforced PEEK, ceramic). Typically, a sleeve may be nitinol or PEEK. In some embodiments, if a sleeve of an implantable device is attached to a head or cannulated rod, it is made of the same material. In some variations, a sleeve is not nitinol. For example, in some variations, if a sleeve of an implantable device is not attached to a head or cannulated rod, it might not include nitinol. Doing so may advantageously reduce device cost.

Figure 22A:
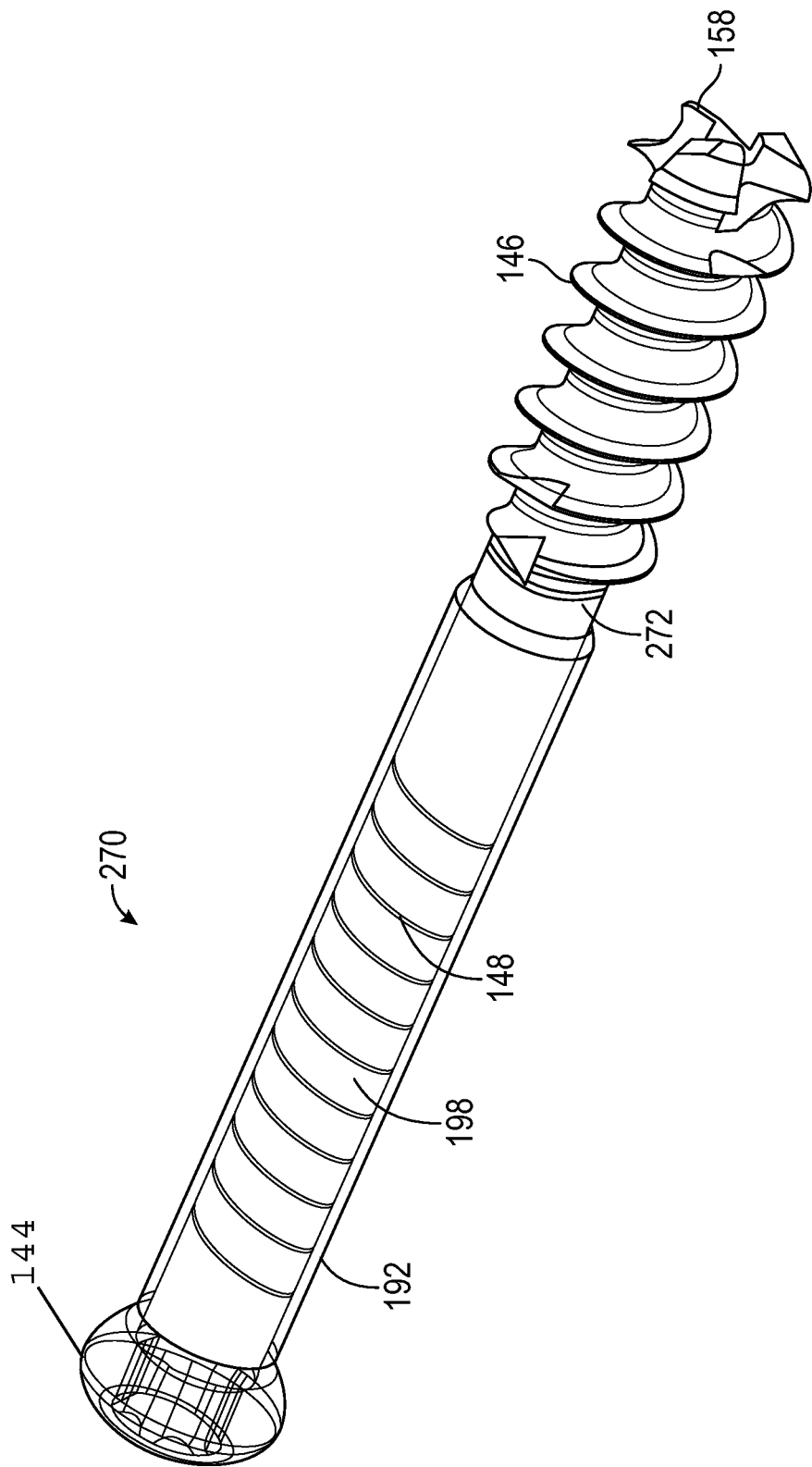
Figure 22C:
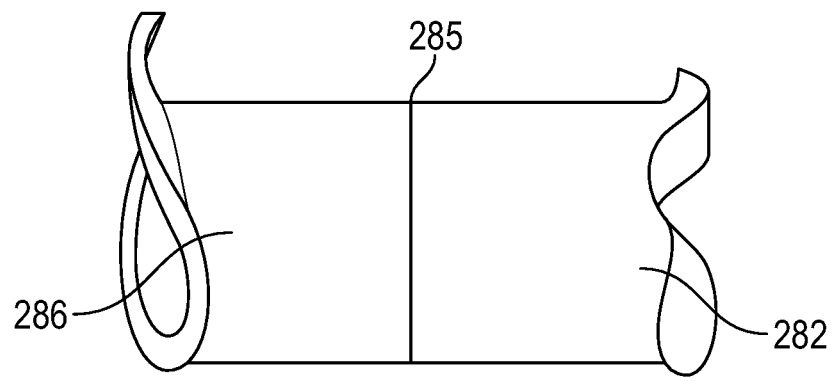
Figure 22D:
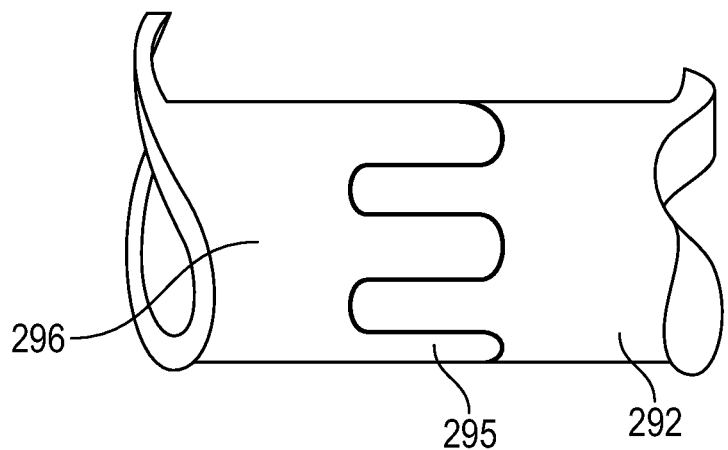
Figure 22E:
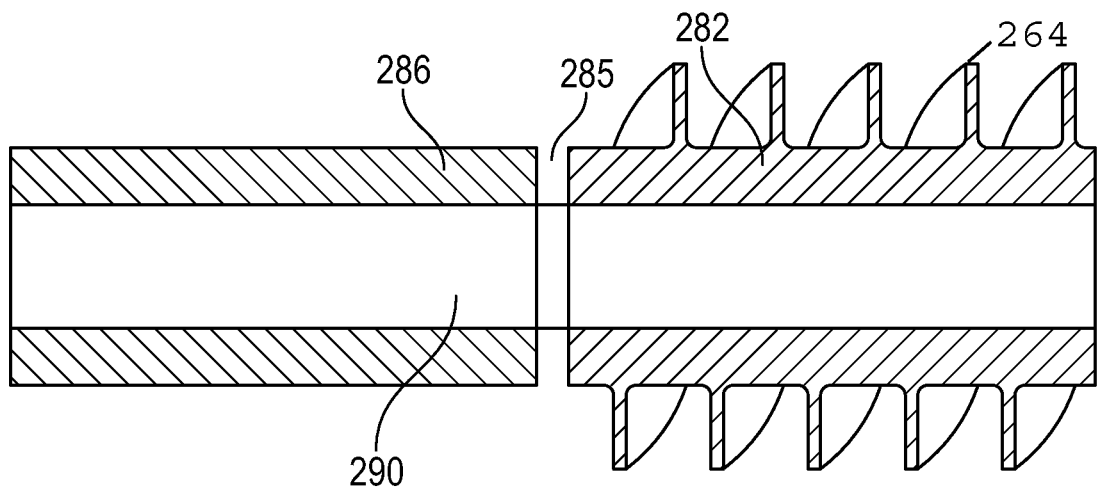

FIGS. 22A-22E show other implantable device with a sleeve and methods of assembling the sleeve over a rod. In one method, a sleeve precursor is placed over a cannulated rod and then a threaded end region is attached to the cannulated rod 272 to form an implantable device. FIG. 22A shows a perspective view of implantable device 270 with sleeve 192 over part of cannulated rod 272. FIG. 22A also shows proximal head 144 and distal threads 146 on the proximal and distal ends, respectively, of implantable device 270. Sleeve 192 is illustrated in this view as semi-transparent in order to show underlying helical cut 148; however sleeve 192 does not need to be and typically will not be semi-transparent. As described elsewhere herein, cannulated rod 272 and other rods herein can have two or more than two helical cuts, such as a double helix, discontinuous helices, etc. FIG. 22B illustrates a system with three pieces ready for assembly and useful for forming implantable device 270. Sleeve precursor 276 is placed over cannulated rod precursor 266 (see arrow labeled "A"). Proximal end 278 of bone engagement part 268 is brought against distal end 280 of cannulated rod precursor 266 (see arrow labeled "B"). Proximal end 278 of bone engagement part 268 can have a first mating feature 284 configured to mate with a second (corresponding) mating feature 288 on distal end 280 of cannulated rod precursor 266. For example, a first mating feature can include a pin at the end of a ledge. First mating feature can be inserted into a hole in the second (corresponding) mating feature, forming tight-fitting parts. The ledge can abut distal end of cannulated rod precursor 266. The locations of the first and second mating features can be reversed (e.g., a hole can be on proximal end 278 of bone engagement part 268 and a pin can be on a second (corresponding) mating feature on distal end 280 of cannulated rod precursor 266). Other mating features can additionally or instead be utilized. FIG. 22C shows an example of a bone engagement part 282 fitted with cannulated rod precursor 286 forming joint 285. Ends of bone engagement part 282 and cannulated rod precursor 286 have similar outer sized diameters such that they form even or flat surfaces when fit together. Ends of bone engagement part 282 and cannulated rod precursor 286 or other embodiments herein may or may not have additional mating features inside (not shown in this view). An outside surface of the bone engagement part 282 and cannulated rod precursor 286 joint is smooth (an outside diameter of bone engagement part 282 is the same size as an outside diameter of distal end of cannulated rod precursor 286). FIG. 22D shows joint 295 between cannulated rod precursor 296 and bone engagement part 292 in which the ends are not flat. The ends have corresponding mating parts, such as notches that fit together. Proximal end (of bone engagement part) and corresponding end (of cannulated rod precursor) can be smooth, not smooth, toothed, not toothed, or regular or irregular. In some variations, the pieces can have corresponding twist-lock ends or a bayonet mount. Proximal end of any bone engagement part (e.g., bone engagement part 292) and distal end of any cannulated rod precursor (e.g., cannulated rod precursor 296) can fastened together, such as by adhering, bonding, gluing, or welding to adhere, bond, glue, or weld the two ends together. FIG. 22E shows assembly aid 290 crossing joint 285. Assembly aid 290 can be a rod configured to align different parts, a part to prevent adhesive or glue from landing on an unwanted area (e.g., an inside wall of the cannulated rod). In this and other embodiments, a portion of a proximal end of a bone engagement part may have an unthreaded portion between the threads and the proximal end, such as shown in FIG. 22E. This may aid in device assembly.

Figure 23A:
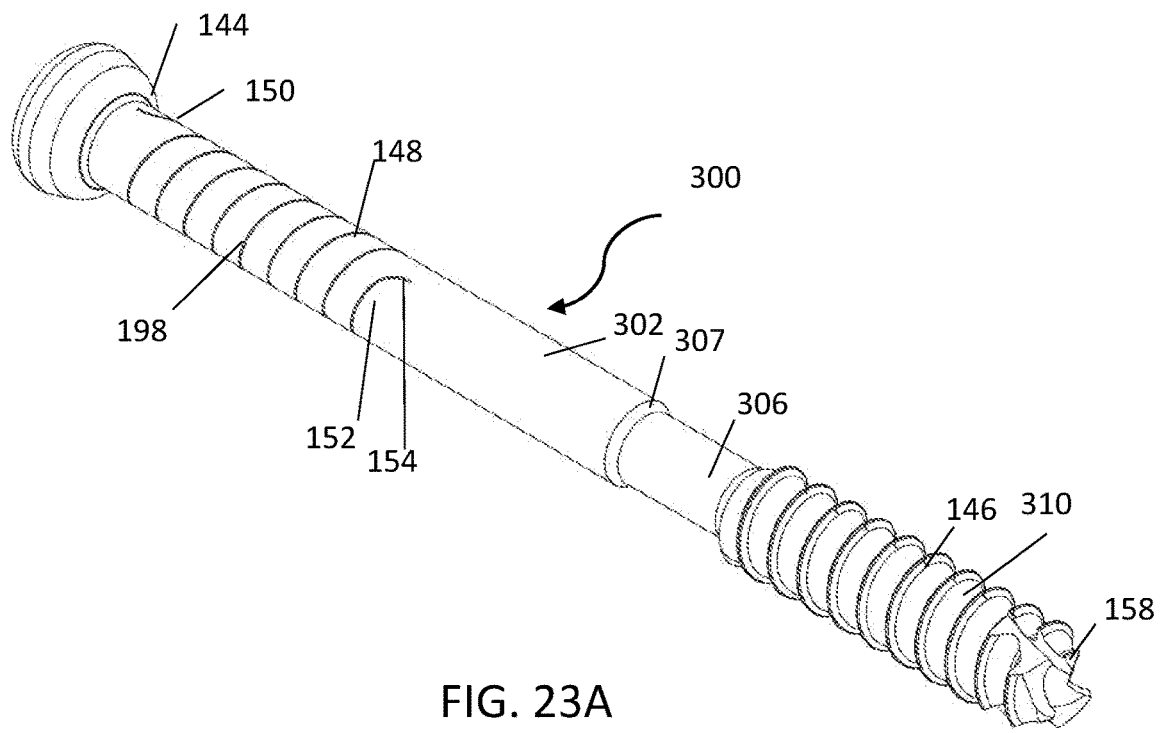
FIG. 23A shows an isometric view of an exemplary implantable device with a step configuration.
Figure 23B:
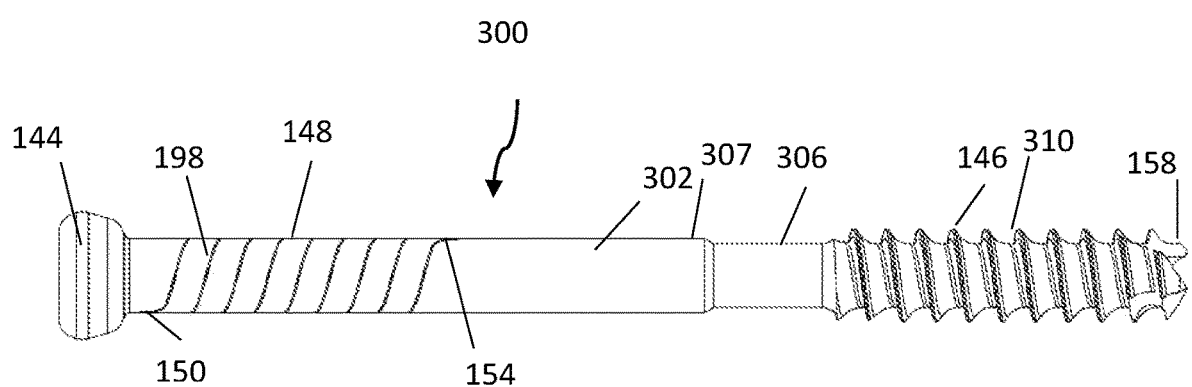
FIG. 23B shows a side view of the implantable device shown in FIG. 23A.

FIG. 23A shows a perspective view of implantable device 300 with a step configuration. FIG. 23B shows a side view of implantable device 300 shown in FIG. 23A. Implantable device 300 has cannulated rod 302 having a dynamic compression portion with helical cut 148. Cannulated rod 302 is attached to or continuous with bone engagement part 310 with step down region 306 through a step-up region 307. Step-down region 306 has a smaller outer diameter than does cannulated rod 302. Step-down region 306 also has a smaller outer diameter than does bone engagement region 310. Cannulated rod 302 may have a thicker wall than does step-down region 306. Step-up region 307 may be beveled or curved. Similar as to described above, the bone engagement or distal anchor feature can transform from a radially compressed shape (e.g., a deformed, shape memory shape) for insertion to a radially expanded shape for anchoring the implant in a bone channel, and the dynamic compression portion can axially extend. The dynamic compression portion is configured to contract from the second elongated configuration towards the first, compact configuration, thereby urging the first bone segment and the second bone segment together.

Figures 24A, 24B:
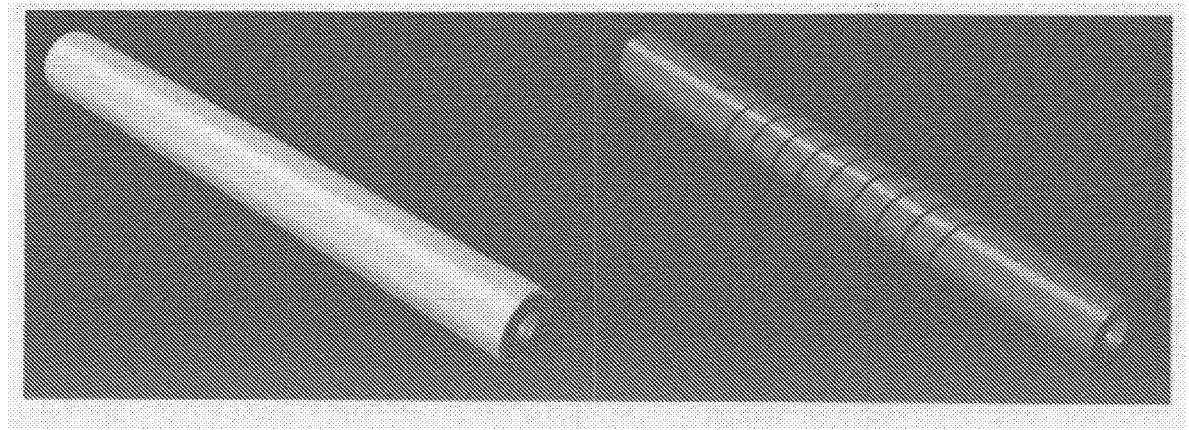
FIG. 24A shows an exemplary sleeve precursor for an implantable device.
FIG. 24B shows an exemplary dynamically changeable helical region.
Figure 24C:
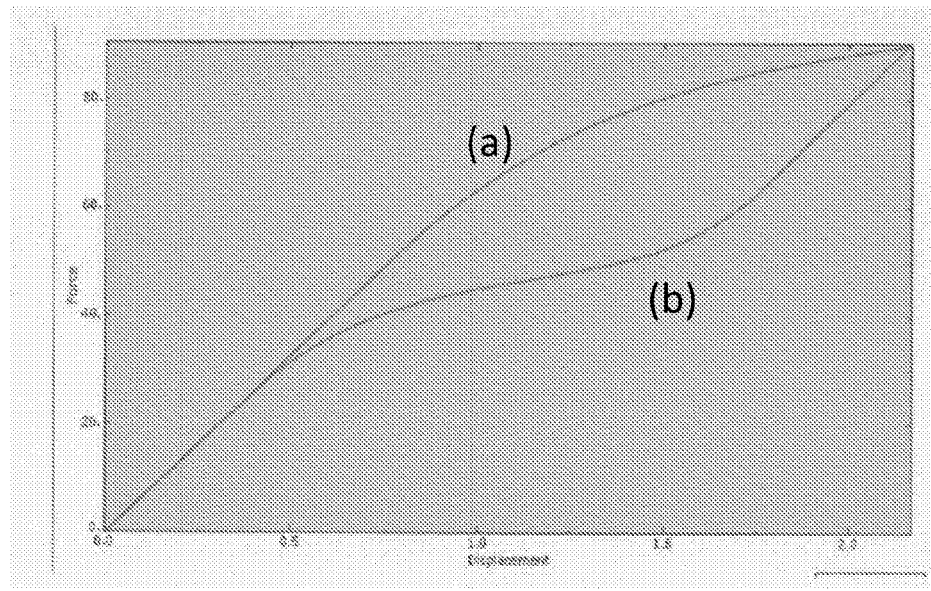
FIG. 24C shows a force displacement graph for the dynamically changeable helical region shown in FIG. 24B with the sleeve precursor shown in FIG. 24A over it.
Figure 24D:
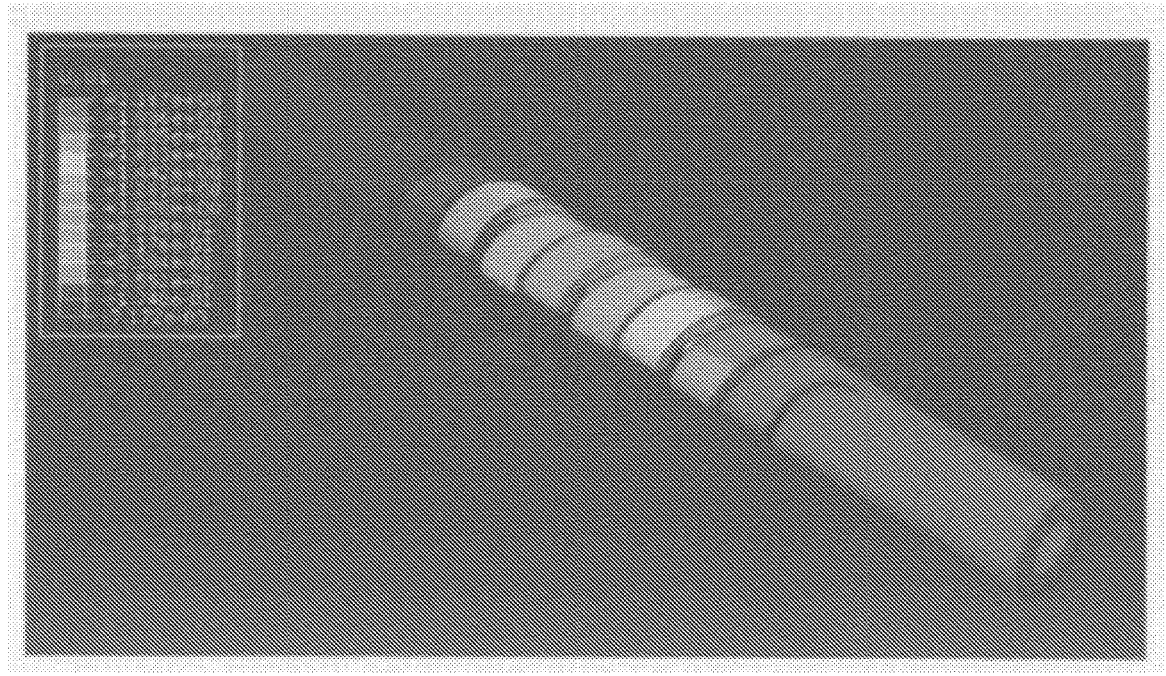
FIG. 24D shows a shaded (false-color) image of a helical region for the dynamically changeable helical region shown in FIG. 24B with the sleeve precursor shown in FIG. 24A over it.

FIGS. 24A-24D show a set-up and results of a torque study for expanding a double helix inside a sleeve. FIG. 24A shows the sleeve and FIG. 24B shows the dynamic compression zone (double helix) that is inside the sleeve for the study. The simulation results are presented for 90 newton axial pull (the inner dynamic compression zone (double helix) was stretched, similar to during device use when a compressive force is applied by the double helix to the bone engagement end. In this example, counterclockwise torque expanded the double helix into the outer sleeve. FIG. 24C shows a force displacement graph for the expanding double helix (shown in FIG. 24B) with the sleeve precursor (shown in FIG. 24A) over it. The double helix shows nitinol hysteresis behavior. Curve (a) in FIG. 24C shows the results from an implant with a double helix undergoing increased displacement (stretched). Curve (b) in FIG. 24C shows the results from an implant with a double helix undergoing decreased displacement (in the opposite direction from curve (a)). Force (N) is shown as a function of displacement (in mm). 90N axial pull gives more than 2 mm of extension (e.g., 2.167 mm of extension). With helix stretch and compression, coil diameter is reduced slightly. FIG. 24D shows a shaded (false-color image) of a helical region for the dynamically changeable helical region shown in FIG. 24B with the sleeve precursor shown in FIG. 24A over it.

Figure 25A:
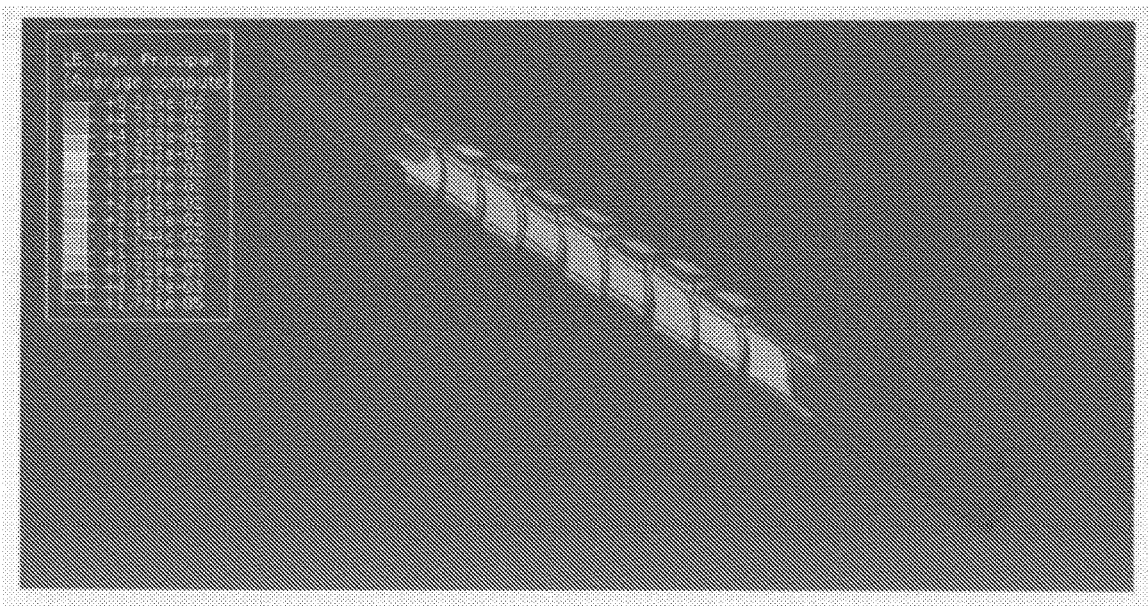
FIG. 25A shows a shaded (false-color) image of a cut-away region of a cannulated rod.
Figure 25B:
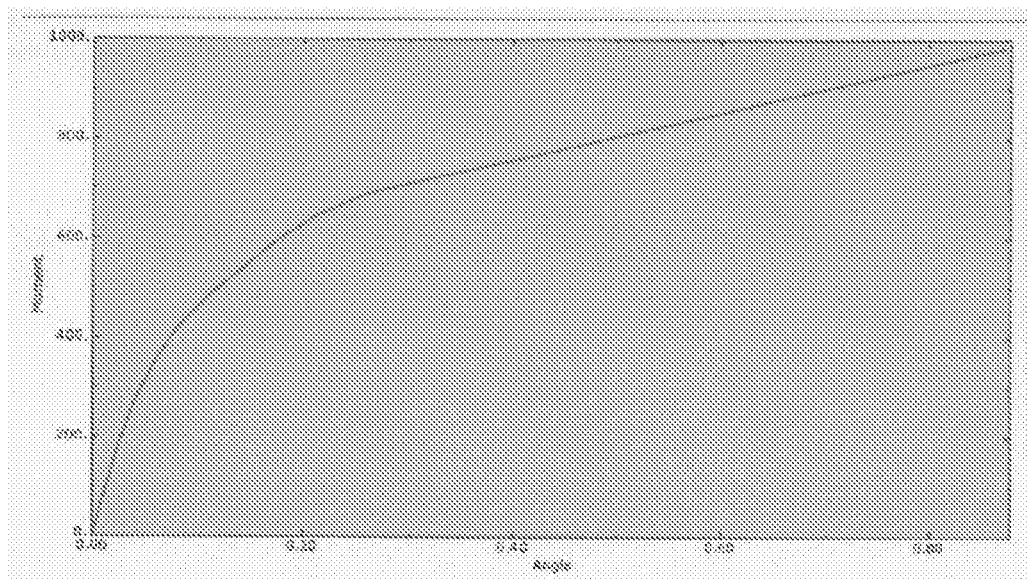
FIG. 25B shows a force-displacement (moment-angle) plot for an exemplary helical region of an implantable device.
Figure 25C:
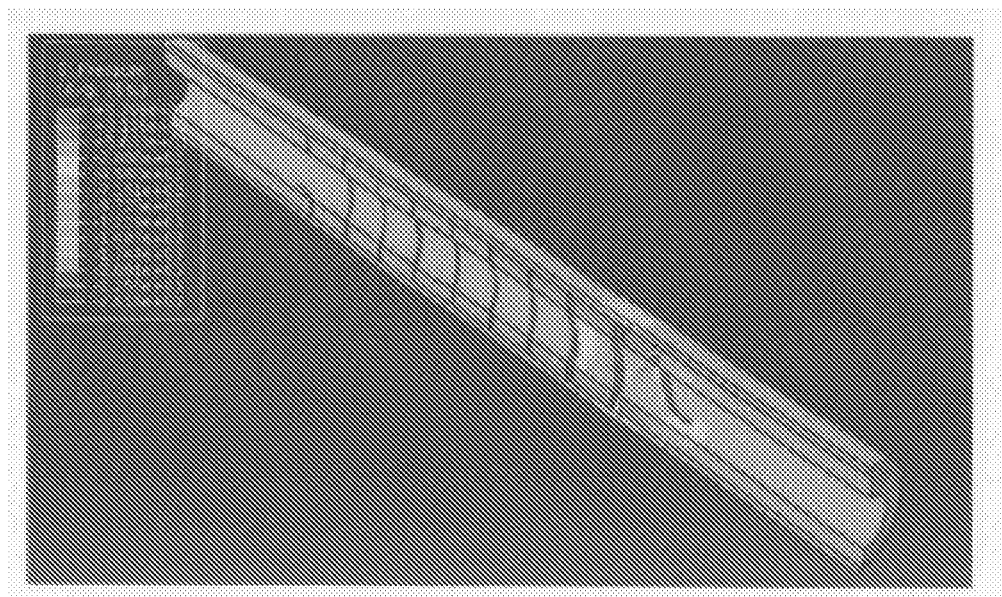
FIG. 25C shows a shaded (false-color) image along an isometric cross-sectional view of a cannulated rod.

FIG. 25A shows a shaded (false-color image) of a cut-away region of the stretched cannulated rod (as described in FIGS. 24A-B). The dynamic compression zone shows about 4% strain at a 90N axial load. The strain is relatively distributed along the length of the dynamic compression zone. FIG. 25B shows a force-displacement (moment-angle) plot for a helical region of an exemplary implantable device with a back-out (e.g., counterclockwise rotation) torque of 1N-M applied. The coils expand and are grabbed by the sleeve at about 0.4 to 0.5 radians, limiting the moment-angle. Angle units in FIG. 25B are in radians. When the helices expand (e.g., expand radially outwards), the angle increases and the helix material in the dynamic compression zone contacts the inside of the sleeve. The greater the angle of the helix(helices), the higher the grip force between the expanding helix (helices) and the inside of the sleeve. FIG. 25C shows stress distribution. FIG. 25C shows a false-color image along an inside of cross-section of a cannulated rod and sleeve with end geometry. At 1N-M of applied torque, the outer sleeve is reacting to the full load. Stress is distributed as the helixes expand radially outward (i.e., perpendicular to the long axis of the implant.

Methods disclosed herein include securing bone segments (e.g., of a broken bone) together using dynamic compression configured to provide compression over a period of from a few hours to days, weeks, months, and/or years. Some methods include the step of introducing an implantable device through a first bone segment and at least partially into a second bone segment. Some methods include predrilling a first channel in the first bone segment and a second channel in the second bone segment. In some methods, the implantable device has an elongate body with a proximal end and a distal end; a head region at the proximal end and wherein the head region engages with a proximal end of the first bone segment (either directly or through a substrate such as a bone plate); a bone engagement part at the distal end wherein the bone engagement part engages with the second bone segment (e.g., an internal surface of a bone channel through the second bone segment); a dynamic compression portion between the head region and the bone engagement part, the dynamic compression portion in a first axially compact configuration.

Some embodiments include the step of transforming the dynamic compression portion into a second axially elongated configuration. Some embodiments include the step of urging the dynamic compression portion from the second elongated configuration towards the first, compact configuration, thereby urging the first bone segment and the second bone segment together. In some embodiments, the dynamic compression portion axially contracts by at least 0.5% relative to the length of the axially compact configuration. In some embodiments, the head region is wider than other portions of the elongate body. Some embodiments include the step of drilling a first channel through the first bone segment and drilling a second channel at least partially through the second bone segment. In some embodiments, the implantable device is configured to axially contract at least 1%, at least 2%, at least 5% or at least 10% relative to the length of the axially compact configuration. Some embodiments include the step of contracting the implantable device by at least 1%, at least 2%, at least 5% or at least 10% relative to the length of the axially elongated configuration toward the axially compact configuration after the implantable device has been introduced into the bone segments. Some embodiments include the step of transforming the bone engagement part of the implant from a radially smaller structure to a radially larger structure and thereby engaging the second bone segment and holding the implantable device in the second bone segment. In some embodiments, the dynamic compression portion includes a hollow region having a helical slit through a wall thickness thereof. In some embodiments, urging includes axially compacting the helical slit. In some embodiments, a diameter of the dynamic compression portion remains relatively constant during the urging step. In some embodiments, the dynamic compression portion and bone engagement part comprise Nitinol. In some embodiments, at least a portion of the head region remains outside the first bone segment. In some embodiments, the head region remains outside the first bone segment. In some embodiments, at least a portion of the head region is within the first bone segment. In some embodiments, the introducing step requires substantially zero insertion force (e.g., the implant may be placed or inserted into (pre-drilled) bone channels without requiring substantial pushing or torquing on the part of the surgeon).

Methods disclosed herein include a method of withdrawing an implantable device from a bone. A method of withdrawing an implantable device may include providing an implantable device (in a bone, bone substitute, bone-like substrate, or another substrate.) The implantable device may include an elongate body with a proximal end and a distal end, wherein the elongate body includes a head region at the proximal end of the elongate body; a bone engagement part at the distal end of the elongate body; a cannulated rod connecting the head region and the bone engagement region, wherein the cannulated rod comprises a dynamic compression portion between the head region and the bone engagement part; and a sleeve over the dynamic compression portion. This and other methods may include the step of rotating the implantable device. In some variations, the step of rotating may include rotating with a removal tool. This and other methods may include the step of stopping, with the sleeve, outward radial expansion of the dynamic compression portion. This and other methods may include the step of withdrawing the implantable device from the bone. In some methods, when withdrawing an implantable device from a substrate (can be naturally occurring bone or synthetic such as an artificial bone-like substrate) the dynamic compression portion is in a second, radially compact configuration. In some methods, an engaging step includes engaging the tool with the head region and the rotating step includes rotating the head region with the tool and thereby rotating the rest of the implantable device. In some methods, the bone engagement part includes an external screw thread, and engaging the tool includes engaging the bone engagement part with the tool, and the method further includes unscrewing the external screw thread from the bone. In some methods of withdrawing an implantable device from a substrate, the tool includes a first tool placed at the proximal end of the elongate body or at the distal end of the elongate body, the method further includes placing a second tool at the distal end of the elongate body or a second tool at the proximal end of the elongate body, respectively, and the method further including engendering relative motion between the first tool and the second tool and thereby rotating the implantable device. Some methods of withdrawing an implantable device from a bone includes the step of stopping, with the sleeve, outward radial expansion of the dynamic compression portion (helical or double helical region(s). Some methods of withdrawing an implantable device from a bone includes the step of preventing, with the sleeve, the dynamic compression portion from contacting an inner wall of the bone. In these and other methods and devices, the sleeve may be maintained over the dynamic compression portion by at least one attachment site between the sleeve and the elongate body. In these and other methods and devices, the sleeve and dynamic compression portion and/or the sleeve and the elongate body and/or the sleeve and the head are not directly attached to one another. Some methods of withdrawing an implantable device from a bone includes the step of (axially) contracting the dynamic compression portion and/or the implantable device by at least 0.5%, at least 1%, at least 2%, at least 3%, at least 4%, at least 5%, at least 6%, at least 7% at least 8%, at least 9%, or at least 10% (relative to a length of the axially elongated configuration.) Some methods of withdrawing an implantable device from a substrate includes the step of (axially) contracting the dynamic compression portion and/or the implantable device by not more than 0.5%, not more than 1%, not more than 2%, not more than 3%, not more than 4%, not more than 5%, not more than 6%, not more than 7% not more than 8%, not more than 9%, or not more than 10%. Some methods of withdrawing an implantable device from a substrate includes the step of transforming the dynamic compression portion in the sleeve from a second, radially compact configuration towards a first, radially expanded configuration. In some methods of withdrawing an implantable device from a substrate, the dynamic compression portion includes a hollow region having one or two helical slits through a wall thickness thereof, and the method further includes axially compacting the helical slit or slits.

Also disclosed herein are methods of making an implantable device, including the step of sliding a sleeve precursor over a distal end of a cannulated rod for an implant and over a dynamic compression portion of the cannulated rod, a proximal end of the cannulated rod connected to a head region, wherein the dynamic compression portion is in either (i) a first axially compact configuration or (ii) a second axially elongated configuration, wherein the dynamic compression portion includes a material configured to transform between the first, compact configuration and the second elongated configuration; fitting a proximal end of a bone engagement element to a distal end of the cannulated rod; and fastening the proximal end of the bone engagement element to the distal end of the cannulated rod, thereby forming an implant including an elongate body with a head region at a proximal end of a cannulated rod, a bone engagement element at a distal end of the cannulated rod, and a sleeve over a central dynamic compression portion therebetween.

In these and other methods, the sleeve precursor includes an elongated hollow channel configured to receive the dynamic compression portion. In these and other methods, the sleeve precursor is a hollow cylinder and open on both ends. In these and other methods, the head region has a larger diameter than a cannulated rod diameter or a sleeve outer diameter, such that the sleeve does not extend over the head. In these and other methods, fitting includes joining a first mating part on the cannulated rod with a corresponding mating part on the bone engagement element. In these and other methods and devices, the mating pieces have a clearance fit, transition fit, or an interference fit. In these and other methods, fastening includes gluing or welding the bone engagement element to the distal end of the cannulated rod. These and other methods include the step of placing a removable rod in an inside of the elongate body prior to the fastening step, performing the fastening step, and removing the removable rod from the implant.

Also disclosed herein are methods of making an implantable device by sliding a sleeve precursor over a proximal end of a cannulated rod for an implant and over a dynamic compression portion of the cannulated rod, a proximal end of the sleeve precursor connected to a head region, wherein the dynamic compression portion is in either (i) a first axially compact configuration or (ii) a second axially elongated configuration, wherein the dynamic compression portion includes a material configured to transform between the first, compact configuration and the second elongated configuration, and wherein a bone engagement region is connected to a distal end of the cannulated rod; and fastening the sleeve precursor and connected head to the cannulated rod, thereby forming the implantable device including an elongate body with a head region at a proximal end of a cannulated rod, a bone engagement element at a distal end of the cannulated rod, and a sleeve over a central dynamic compression portion therebetween.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising." when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An implantable device comprising:
    an elongate body with a proximal end and a distal end, the elongate body comprising:
        a head region at the proximal end of the elongate body;
        a bone engagement part at the distal end of the elongate body;
        a cannulated rod connecting the head region and the bone engagement region, wherein the cannulated rod comprises a dynamic compression portion between the head region and the bone engagement part, the dynamic compression portion in either (i) a first axially compact configuration or (ii) a second axially elongated configuration, wherein the dynamic compression portion comprises a material configured to transform between the first, axially compact configuration and the second, axially elongated configuration; and
    a sleeve over the dynamic compression portion, the sleeve having a proximal end and a distal end,
    wherein, when the dynamic compression portion is in (i) the first axially compact configuration, the sleeve contacts the dynamic compression portion and prevents outward radial expansion of the dynamic compression portion, and when the dynamic compression portion is in (ii) the second axially elongated configuration, the implantable device comprises a gap of at least 0.002 inches between the dynamic compression portion and an inside diameter of the sleeve.

2. The implantable device of claim 1, wherein an outside diameter of the dynamic compression portion and an inside diameter of the sleeve are not more than 0.020 inches apart.

3. The implantable device of claim 1, wherein the sleeve substantially surrounds an outside of the dynamic compression portion.

4. The implantable device of claim 1, wherein the sleeve is attached to the elongate body.

5. The implantable device of claim 1, wherein the sleeve is attached to the cannulated rod.

6. The implantable device of claim 1, wherein the proximal end of the sleeve is attached to a proximal end of the elongate body.

7. The implantable device of claim 1, wherein the distal end of the sleeve is attached to the distal end of the elongate body.

8. The implantable device of claim 1, wherein the sleeve is not attached to the elongate body and the sleeve is configured to move over the elongate body.

9. The implantable device of claim 1, wherein the dynamic compression zone and bone engagement part comprise a shape memory material.

10. The implantable device of claim 1, wherein the dynamic compression zone and bone engagement part comprise nitinol.

11. The implantable device of claim 1, wherein the sleeve comprises nitinol.

12. The implantable device of claim 1, wherein the sleeve comprises titanium or PEEK.

13. The implantable device of claim 1, wherein the sleeve does not comprise nitinol.

14. The implantable device of claim 1, wherein the cannulated rod comprises a rod wall and a first helical slit through the rod wall.

15. The implantable device of claim 14, wherein the cannulated rod comprises a second helical slit in the rod wall.

16. The implantable device of claim 15, wherein the first and second helical slits are wrapped around a single length of a central zone of the dynamic compression portion, further wherein the dynamic compression portion is separated from the bone engagement part by an unthreaded intervening portion therebetween.

17. The implantable device of claim 1, wherein the dynamic compression portion further comprises (i) a first, radially compact configuration or (ii) a second, radially expanded configuration, wherein the material in the dynamic compression portion is configured to transform between the first, radially compact configuration and the second radially expanded configuration.

18. The implantable device of claim 1, wherein a diameter of the cannulated rod is smaller than a diameter of the bone engagement part at the distal end of the elongate body.

19. An implantable device comprising:
    an elongate body with a proximal end and a distal end, the elongate body comprising:
        a head region at the proximal end of the elongate body;
        a bone engagement part at the distal end of the elongate body;
        a cannulated rod connecting the head region and the bone engagement region, wherein the cannulated rod comprises a dynamic compression portion between the head region and the bone engagement part, the dynamic compression portion in either (i) a first axially compact configuration or (ii) a second axially elongated configuration, wherein the dynamic compression portion comprises a material configured to transform between the first, axially compact configuration and the second, axially elongated configuration; and a sleeve over the dynamic compression portion, the sleeve having a proximal end and a distal end, wherein the bone engagement part comprises a screw thread configured to anchor the implantable device into a bone segment, wherein the second, elongated configuration is at least 0.5% longer than the first, compact configuration, wherein the dynamic compression portion comprises a cannulated rod with a rod wall and a helical slit through a wall thickness thereof, wherein the helical slit is provided with an end geometry that is different from a middle portion of the helical slit, wherein the end geometry includes a curved portion and a straight portion, and the straight portion generally aligns with a longitudinal axis of the implantable device, and the curved portion transitions a trajectory of the helical slit between a normal pitch to a direction of the straight portion, wherein the curved portion and the straight portion cooperate to dissipate stresses that may be concentrated at an end of the helical cut, wherein, when the dynamic compression portion is in (i) the first axially compact configuration, the sleeve contacts the dynamic compression portion and prevents outward radial expansion of the dynamic compression portion, and when the dynamic compression portion is in (ii) the second axially elongated configuration, the implantable device comprises a gap of at least 0.002 inches between the dynamic compression portion and an inside diameter of the sleeve.

* * * * *